United States Patent
Tanaka et al.

(10) Patent No.: US 10,227,337 B2
(45) Date of Patent: Mar. 12, 2019

(54) EVALUATION PROBE FOR CENTRAL NERVOUS SYSTEM PERMEABILITY, EVALUATION METHOD FOR CENTRAL NERVOUS SYSTEM PERMEABILITY, AND SCREENING METHOD USING AN EVALUATION PROBE FOR CENTRAL NERVOUS SYSTEM PERMEABILITY

(75) Inventors: Toshio Tanaka, Tsu (JP); Kohei Watanabe, Yokohama (JP); Tsuyoshi Nomoto, Tokyo (JP); Mie Okano, Moriya (JP); Taichi Shintou, Saitama (JP); Takeshi Miyazaki, Yokohama (JP); Yuhei Nishimura, Tsu (JP); Yasuhito Shimada, Tsu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1610 days.

(21) Appl. No.: 13/397,759

(22) Filed: Feb. 16, 2012

(65) Prior Publication Data
US 2012/0207683 A1    Aug. 16, 2012

(30) Foreign Application Priority Data

Feb. 16, 2011  (JP) ................. 2011-030778
Aug. 30, 2011  (JP) ................. 2011-187500

(51) Int. Cl.
| C07D 417/06 | (2006.01) |
| C07D 417/14 | (2006.01) |
| C09B 23/04  | (2006.01) |
| C09B 23/06  | (2006.01) |
| G01N 33/50  | (2006.01) |

(52) U.S. Cl.
CPC ......... *C07D 417/06* (2013.01); *C07D 417/14* (2013.01); *C09B 23/04* (2013.01); *C09B 23/06* (2013.01); *G01N 33/5082* (2013.01); *G01N 33/5088* (2013.01); *G01N 2333/4603* (2013.01); *G01N 2800/28* (2013.01)

(58) Field of Classification Search
CPC .... C07D 417/06; C07D 417/14; C09B 23/04; C09B 23/06; G01N 33/5082; G01N 33/5088; G01N 2800/28; G01N 2333/4603
See application file for complete search history.

(56) References Cited

U.S. PATENT DOCUMENTS

| 2006/0193776 A1 | 8/2006  | Goldsmith et al. |
| 2011/0182810 A1 | 7/2011  | Nomoto et al.    |
| 2011/0189096 A1 | 8/2011  | Watanabe et al.  |
| 2011/0236310 A1 | 9/2011  | Watanabe et al.  |
| 2011/0243850 A1 | 10/2011 | Shintou et al.   |
| 2013/0280169 A1 | 10/2013 | Watanabe et al.  |
| 2014/0017722 A1 | 1/2014  | Watanabe et al.  |

FOREIGN PATENT DOCUMENTS

| EP | 2 399 612 A1    | 12/2011 |
| JP | 2006-121981 A   | 5/2006  |
| JP | 2007-525665 A   | 9/2007  |
| JP | 2009-250652 A   | 10/2009 |
| JP | 2010-168369 A   | 8/2010  |
| WO | 2005/080974 A1  | 9/2005  |
| WO | 2010/074325 A1  | 7/2010  |
| WO | 2010/074326 A1  | 7/2010  |

OTHER PUBLICATIONS

"Retina," Jul. 7, 2016, https://en.wikipedia.org/wiki/Retina.*
"Nerve Fiber Layer," Jun. 29, 2016, https://en.wikipedia.org/wiki/Nerve_fiber_layer.*
"Optic Nerve," Jul. 18, 2016, https://en.wikipedia.org/wiki/Optic_nerve.*
Jae-Yeon Jeong et al., "Functional and Developmental Analysis of the Blood-Brain Barrier in Zebrafish," 75(5) Brain Research Bulletin 619-628 (Mar. 2008).
Jing Xie et al., "A Novel Transgenic Zebrafish Model for Blood-Brain and Blood-Retinal Barrier Development," BMC Developmental Biology 10:76, pp. 1-14 (Jul. 2010) (XP021072137).
Extended European Search Report in European Application No. 12001025.1 (dated Jun. 1, 2012).
Non-final Office Action in U.S. Appl. No. 13/133,357 (dated Jun. 2, 2014).
Non-final Office Action in U.S. Appl. No. 13/133,381 (dated Jun. 2, 2014).

(Continued)

*Primary Examiner* — Michael G. Hartley
*Assistant Examiner* — Leah H Schlientz
(74) *Attorney, Agent, or Firm* — Venable LLP

(57) ABSTRACT

Provided is an evaluation probe capable of optically evaluating permeability of a substance through a central nervous system tissue. Also provided is an evaluation method for permeability of a substance through a central nervous system tissue using an evaluation probe for central nervous system permeability. Also provided is a screening method using an evaluation probe for central nervous system permeability. The evaluation probe for central nervous system permeability includes, as an active ingredient, at least one kind of compound represented by the following general formula (1).

General formula (1)

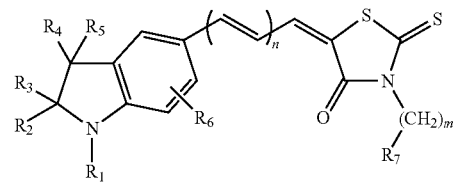

12 Claims, 3 Drawing Sheets

(56) References Cited

OTHER PUBLICATIONS

Ariane Jansma et al., "Automated Microflow NMR: Routine Analysis of Five-Microliter Samples," 77 Anal. Chem. 6509-6515 (Aug. 2005).
Watanabe et al., U.S. Appl. No. 13/938,915, filed Jul. 10, 2013.
Watanabe et al., U.S. Appl. No. 15/244,835, filed Aug. 23, 2016.
Communication pursuant to Article 94(3) EPC in European Application No. 12 001 025.1 (dated Nov. 2, 2018).

* cited by examiner

EVALUATION PROBE FOR CENTRAL NERVOUS SYSTEM PERMEABILITY, EVALUATION METHOD FOR CENTRAL NERVOUS SYSTEM PERMEABILITY, AND SCREENING METHOD USING AN EVALUATION PROBE FOR CENTRAL NERVOUS SYSTEM PERMEABILITY

BACKGROUND OF THE INVENTION

Field of the Invention

The present invention relates to an evaluation probe capable of optically evaluating permeability of a substance through a central nervous system (hereinafter, also referred to as "CNS") tissue, an evaluation method for permeability of a substance through a CNS tissue using the evaluation probe for CNS permeability, and a screening method using the evaluation probe for CNS permeability.

Description of the Related Art

Barriers (blood-nerve barriers) are present in CNS tissues such as brain and retina of vertebrates and they restrict permeation of a substance to the CNS tissues. As the barriers present in the CNS tissues, there are known, for example, a blood-brain barrier (BBB), a blood-cerebrospinal fluid barrier (BCSFB), and a blood-retinal barrier (BRB). In those barriers, capillary endothelium cells of the CNS tissues form a tight junction, and thereby diffusion of a substance via an intercellular gap hardly occurs. Further, a wide range of involvement of transporters to the barriers are known, and it has been clarified that there exist a transporter involved in influx transport from blood to brain, and a transporter involved in efflux transport from brain to blood.

The transporters are distributed in organs and tissues throughout the body, and they are divided into two families, i.e., an ATP binding cassette (ABC) family, which carries out transport by utilizing hydrolysis energy of ATP, and a solute carrier (SLC) family, which carries out transport without using energy of ATP. In a human, 48 kinds of ABC transporter genes and 319 kinds of SLC transporter genes have been identified heretofore. The transporters include an influx transporter, which is responsible for an influx function for a drug into cells, and an efflux transporter, which is responsible for an efflux function for a drug from cells.

It is important in elucidation of various pathological conditions and discovery and development of drugs to evaluate a substance transport function via a transporter, and to examine or screen an action of a substance such as an inhibitor having an influence on a function of a transporter.

For example, it is said that a disease caused by transporter abnormality increases with age, and such abnormalities of transporters are associated with about 10% of genes associated with diseases in people aged 50 or more. It can be said that a pathological condition associated with a transporter is a pathological condition caused by membrane transport disorder due to transporter abnormality. Hence, it is conceivable that the transporter can serve as a target molecule for development of a therapeutic drug for the so-called lifestyle-related disease.

On the other hand, in drug delivery, development of a drug that is recognized by the influx transporter or is hardly recognized by the efflux transporter is a possible strategy. In various tissues, in particular, out of the efflux transporters each having an efflux function for a drug from cells, a multidrug efflux transporter, which transports a number of anti-cancer agents and the like, is known to exist. The multidrug efflux transporter causes ineffectiveness of a number of drugs for cancer cells and the like, i.e. multidrug-resistance. In view of the foregoing, inhibition of a function of a drug efflux transporter can contribute to growth inhibition of cancer cells through achievement of drug delivery to a target tissue or an increase in intracellular concentration of an anti-cancer agent or the like.

Japanese Patent Application Laid-Open No. 2009-250652 discloses a screening method including bringing a labeled substance to be tested into contact with cells and measuring the labeled substance in the cells with time. According to this method, a rate or the like of transport of the substance to be tested via a transporter or the like can be quantified by detecting the labeled substance.

Japanese Patent Application Laid-Open No. 2006-121981 discloses a screening method for an inhibitor for MRP1, a multidrug-resistant protein, including: administering a substance to be tested to a nematode having introduced therein a human mrp1 gene as a multidrug efflux transporter; and detecting formation of a drug-resistant larva of the nematode. Through the use of this method, a substance having an inhibitory effect on MRP1, a multidrug-resistant protein, can be screened.

Japanese Patent Translation Publication No. 2007-525665 discloses a technology for using zebrafish in screening a blood-brain barrier. In recent years, it has been clarified that a barrier in a CNS tissue is found in zebrafish as a small bony fish as well. The literature discloses a method including evaluating an inhibitory effect of P-glycoprotein (Pgp) on rhodamine 123 distribution including: injecting rhodamine 123, a fluorescent dye, into the pericardium of a zebrafish larva exposed to verapamil, an inhibitor for Pgp; and quantifying fluorescence in the brain. In this method, since zebrafish, which has a high homology to a human, is used, an experiment with consideration of an influence of a sophisticated biological mechanism such as an in vivo metabolism mechanism can be carried out.

Meanwhile, Japanese Patent Application Laid-Open No. 2010-168369 discloses a staining composition for an intraocular tissue capable of staining a retinal tissue as a CNS tissue by being simply exposed to a living individual organism such as zebrafish. The reference also discloses a screening method for an effect, a side effect, or safety of a chemical substance on an intraocular tissue.

SUMMARY OF THE INVENTION

However, in the method of Japanese Patent Application Laid-Open No. 2009-250652, it is necessary to label a tested substance which is to be brought into contact with cells, and hence it is difficult to screen numerous target substances simultaneously.

Further, in the method of Japanese Patent Application Laid-Open No. 2006-121981, a nematode, having preliminarily introduced a gene for a transporter serving as a target, is used, which corresponds to an experimental system in which an influence of a sophisticated biological mechanism such as a blood-nerve barrier or an in vivo metabolism mechanism of a higher animal is omitted. Thus, the resultant information is limited. Also in Japanese Patent Translation Publication No. 2007-525665, influences of some sophisticated biological mechanisms are omitted through inhibition of an efflux transporter function. Thus, the resultant information may become limited to some extent.

In addition, in the method of Japanese Patent Translation Publication No. 2007-525665, a probe for functional evaluation of a transporter (rhodamine 123) needs to be injected into pericardium. Such high invasiveness may serve as an artifact and may have an influence on reproducibility of the results.

In view of those problems, according to an exemplary embodiment of the present invention, there is provided a technology capable of simply evaluating substance transport via a transporter by a less-invasive method in a system with consideration of an influence of a sophisticated biological mechanism such as an in vivo metabolism mechanism as well.

The inventors of the present invention have made intensive studies in order to solve the problems. As a result, the inventors have found that a dye compound represented by the following general formula (1) permeate into a living body by being simply exposed to a biological specimen, and serves as a substrate for a transporter associated with at least one of influx and efflux of a substance to central nervous system tissues (cranial nerve tissue, spinal cord, and retina), and have also found such a novel evaluation probe for central nervous system permeability including the compound as to allow functional evaluation of a transporter and evaluation and screening of a compound having an influence on an action of a transporter.

Further, the inventors of the present invention have developed an evaluation method for permeability of a substance through a central nervous system tissue using an evaluation probe for central nervous system permeability, and a screening method using an evaluation probe for central nervous system permeability.

That is, an evaluation probe for central nervous system permeability of the present invention includes, as an active ingredient, at least one kind of compound represented by the following general formula (1).

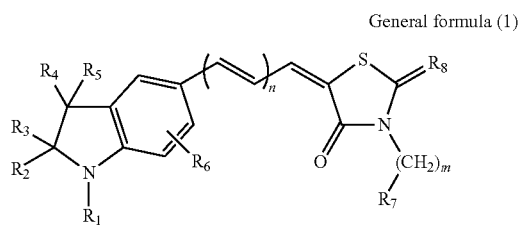

General formula (1)

Here, in the general formula (1): $R_1$ represents one of a hydrogen atom, an alkyl group, an aralkyl group, an alkenyl group, a substituted alkenyl group, a cycloalkenyl group, a cycloalkyl group, an aryl group, a substituted aryl group, a heterocyclic group, and an alkanoyl group; $R_2$ to $R_5$ each independently represent one of a hydrogen atom, an alkyl group, an aryl group, a carboxylic acid group, an alkoxycarbonyl group, and an alkanoyl group, provided that $R_2$ and $R_4$ may be bonded to each other to form a ring; $R_6$ represents one of a hydrogen atom and a halogen atom; $R_7$ represents one of an alkoxycarbonyl group, a carboxylic acid and a salt thereof; $R_6$ represents one of a sulfur atom or a ring represented by the following general formula (2); n represents an integer of 0 to 3; and m represents an integer of 1 or more.

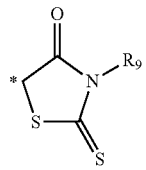

General formula (2)

Here, in the general formula (2): $R_9$ represents one of an alkyl group, an aralkyl group, an alkenyl group, and an aryl group; and "*" represents a bonding site.

According to the present invention, it is possible to provide the novel evaluation probe for CNS permeability. The evaluation probe allows substance transport via a transporter to be simply evaluated by a less-invasive method in an experimental system taken in consideration of an influence of a sophisticated biological mechanism such as an in vivo metabolism mechanism, which has been hitherto difficult. Further, the evaluation probe allows a function of a transporter associated with at least one of influx and efflux in CNS tissues (cranial nerve tissue, spinal cord, and retina) to be evaluated, and allows a compound having an influence on an action of a transporter to be evaluated and screened in a simple and highly reproducible manner. In addition, the evaluation method and the screening method each using the evaluation probe for CNS permeability of the present invention can serve as novel tools effective not only for research on barriers in the CNS and discovery and development of drugs with CNS tissue permeability but also for evaluation and screening of a compound such as an inhibitor having an influence on a transporter.

Further features of the present invention will become apparent from the following description of exemplary embodiments with reference to the attached drawings.

DESCRIPTION OF THE EMBODIMENTS

Figure 1:
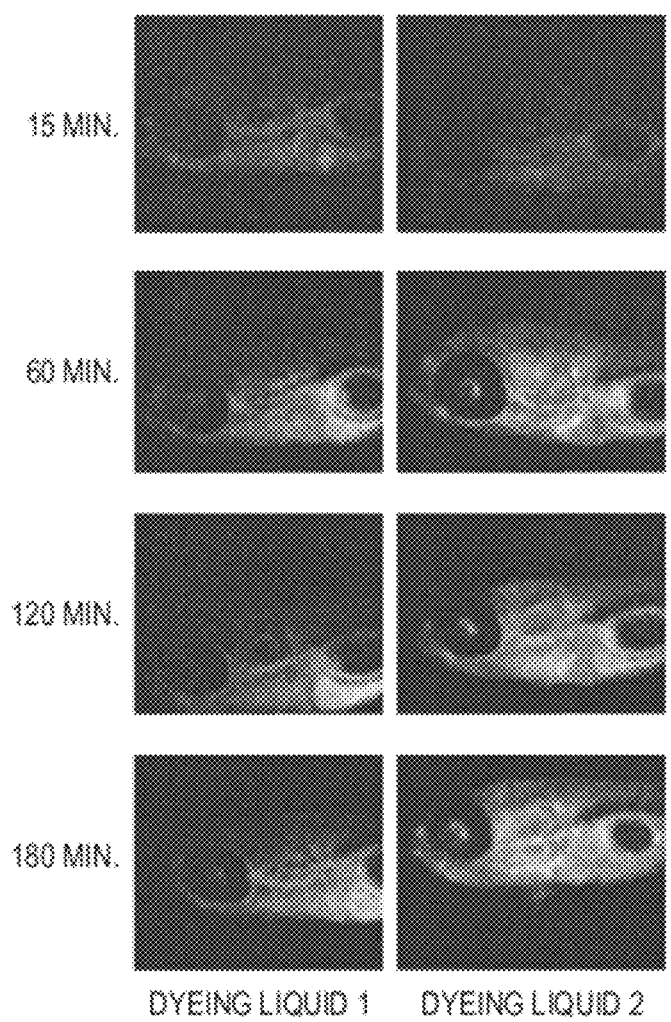
FIG. 1 shows observation images of central nervous system tissues stained with a staining liquid 1 and a staining liquid 2 observed with time in Example 1.

Hereinafter, embodiments of the present invention are described. It should be noted that the embodiments to be disclosed separately are merely illustrative of an evaluation probe for CNS permeability, an evaluation method for CNS permeability, and a screening method using an evaluation probe for CNS permeability according to the present invention. The present invention is by no means limited thereto.

First Embodiment

An evaluation probe for CNS permeability according to a first embodiment of the present invention includes at least one kind of compound represented by the following general formula (1) as an active ingredient.

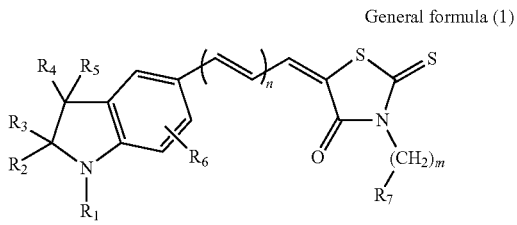

General formula (1)

Here, in the general formula (1): $R_1$ represents one of a hydrogen atom, an alkyl group, an aralkyl group, an alkenyl group, a substituted alkenyl group, a cycloalkenyl group, a cycloalkyl group, an aryl group, a substituted aryl group, a heterocyclic group, and an alkanoyl group; $R_2$ to $R_5$ each independently represent one of a hydrogen atom, an alkyl group, an aryl group, a carboxylic acid group, an alkoxycarbonyl group, and an alkanoyl group, provided that $R_2$ and $R_4$ may be bonded to each other to form a ring; $R_6$ represents one of a hydrogen atom and a halogen atom; $R_7$ represents one of an alkoxycarbonyl group, a carboxylic acid and a salt thereof; $R_8$ represents one of a sulfur atom or a ring represented by the following general formula (2); n represents an integer of 0 to 3; and m represents an integer of 1 or more.

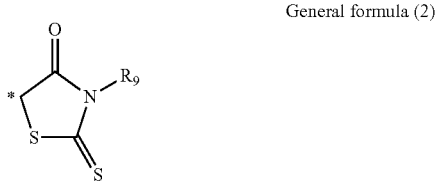

General formula (2)

Here, in the general formula (2): $R_9$ represents one of an alkyl group, an aralkyl group, an alkenyl group, and an aryl group; and "*" represents a bonding site.

Examples of the alkyl group represented by $R_1$ in the general formula (1) include, but not particularly limited to, a methyl group, an ethyl group, a propyl group, a butyl group, and a 3-hexyl group. Each of those groups may further have a substituent as long as the storage stability of the dye compound is not remarkably inhibited.

Examples of the cycloalkyl group represented by $R_1$ in the general formula (1) include, but not particularly limited to, a cyclohexyl group. Each of those groups may further have a substituent as long as the storage stability of the dye compound is not remarkably inhibited.

Examples of the aralkyl group represented by $R_1$ in the general formula (1) include, but not particularly limited to, a benzyl group and a phenethyl group.

Examples of the alkenyl group, substituted alkenyl group, and cycloalkenyl group represented by $R_1$ in the general formula (1) include, but not particularly limited to, a vinyl group, a 2,2-diphenylvinyl group, a 3-butenyl group, and a cyclohexenyl group.

Examples of the aryl group and substituted aryl group represented by $R_1$ in the general formula (1) include, but not particularly limited to, a phenyl group, a 4-bromophenyl group, a 4-methoxyphenyl group, a 4-thiomethylphenyl group, a 6-methoxy-2-naphthyl group, and a naphthyl group.

Each of those groups may further have a substituent as long as the storage stability of the dye compound is not remarkably inhibited.

Examples of the heterocyclic group represented by $R_1$ in the general formula (1) include, but not particularly limited to, a pyridyl group, a pyrazyl group, and a morpholinyl group.

Examples of the alkanoyl group represented by $R_1$ in the general formula (1) include, but not particularly limited to, an acetyl group, a propionyl group, a butyryl group, a pentanoyl group, a benzoyl group, a 1-naphthoyl group, and a 2-naphthoyl group.

$R_1$ in the general formula (1) preferably represents one of an alkyl group, an aralkyl group, and an aryl group, particularly preferably one of a methyl group, an ethyl group, a propyl group, a benzyl group, a phenyl group, a 4-bromophenyl group, a 4-methoxyphenyl group, a 4-thiomethylphenyl group, and a 6-methoxy-2-naphthyl group from the view point of evaluating the permeation of a substance through a CNS tissue.

Examples of the alkyl group represented by each of $R_2$ to $R_5$ in the general formula (1) include, but not particularly limited to, a methyl group, an ethyl group, a propyl group, a butyl group, a cyclohexyl group, and a 3-hexanyl group. Each of those groups may further have a substituent as long as the storage stability of the dye compound is not remarkably inhibited. In particular, it is preferred that $R_2$ to $R_5$ each represent one of a hydrogen atom and a methyl group from the view point of evaluating the permeation of a substance through a CNS tissue.

Examples of the aryl group represented by each of $R_2$ to $R_5$ in the general formula (1) include, but not particularly limited to, a phenyl group and a naphthyl group. Each of those groups may further have a substituent as long as the storage stability of the dye compound is not remarkably inhibited.

Examples of the alkoxycarbonyl group represented by each of $R_2$ to $R_5$ in the general formula (1) include, but not particularly limited to, a methoxycarbonyl group, an ethoxycarbonyl group, a propoxycarbonyl group, and a butoxycarbonyl group.

Examples of the alkanoyl group represented by each of $R_2$ to $R_5$ in the general formula (1) include, but not particularly limited to, an acetyl group, a propionyl group, a butyryl group, a pentanoyl group, a benzoyl group, a 1-naphthoyl group, and a 2-naphthoyl group.

When $R_2$ and $R_4$ are bonded to each other to form a ring, examples of the ring include, but not particularly limited to, saturated aliphatic rings such as a cyclooctane ring, a cycloheptane ring, a cyclohexane ring, a cyclopentane ring, and a cyclobutane ring, partially saturated aliphatic rings such as a cyclopentene ring and a cyclohexene ring, and aromatic rings such as a benzene ring. Each of those rings may further have a substituent as long as the storage stability of the dye compound is not remarkably inhibited.

In particular, when $R_2$ and $R_4$ are bonded to each other to form a ring, it is preferred that the ring be one of a cyclopentane ring and a benzene ring from the view point of evaluating the permeability of a substance through a CNS tissue.

Examples of the halogen atom represented by $R_6$ in the general formula (1) include a fluorine atom, a chlorine atom, a bromine atom, and an iodine atom.

It is preferred that $R_6$ represent one of a hydrogen atom and a bromine atom.

Examples of the alkoxycarbonyl group represented by $R_7$ in the general formula (1) include, but not particularly limited to, a methoxycarbonyl group, an ethoxycarbonyl group, a propoxycarbonyl group, and a butoxycarbonyl group.

Examples of the salt of the carboxylic acid represented by $R_7$ in the general formula (1) include, but not particularly limited to: alkali metal salts such as a sodium salt and a potassium salt; alkaline earth salts such as a magnesium salt and a calcium salt; amine salts such as an ammonium salt, a pyridinium salt, a piperidinium salt, and a triethylammonium salt; and amino acid salts such as a tryptophan salt, a lysine salt, a leucine salt, a phenylalanine salt, a valine salt, and an arginine salt. In particular, a sodium salt, a potassium salt, an ammonium salt, a pyridinium salt, a piperidinium salt, or the like is preferred.

It is preferred that $R_7$ represent one of a carboxylic acid, ethyl carboxylate, a sodium carboxylate, and a potassium carboxylate from the view point of evaluating the permeation of a substance through a CNS tissue.

Examples of the alkyl group represented by $R_9$ in the general formula (2) include, but not particularly limited to, a methyl group, an ethyl group, a propyl group, a butyl group, and a 3-hexanyl group. Each of those groups may further have a substituent as long as the storage stability of the dye compound is not remarkably inhibited.

Examples of the aralkyl group represented by $R_9$ in the general formula (2) include, but not particularly limited to, a benzyl group and a phenethyl group.

Examples of the alkenyl group, substituted alkenyl group, and cycloalkenyl group represented by $R_9$ in the general formula (2) include, but not particularly limited to, a vinyl group, a 2,2-diphenylvinyl group, a 3-butenyl group, and a cyclohexenyl group.

Examples of the aryl group represented by $R_9$ in the general formula (2) include, but not particularly limited to, a phenyl group and a naphthyl group. Each of those groups may further have a substituent as long as the storage stability of the dye compound is not remarkably inhibited.

It is preferred that $R_8$ in the general formula (1) represents a sulfur atom from the view point of evaluating the permeation of a substance through a CNS tissue.

n in the general formula (1) represents an integer of 0 to 3. It is particularly preferred that n represent one of 0 and 1 from the view point of evaluating the permeability of a substance through a CNS tissue.

m in the general formula (1) represents an integer of 1 or more. It is preferred that m represents an integer of 1 to 5, and it is particularly preferred that m represents 1 or 2 from the view point of evaluating the permeability of a substance through a CNS tissue.

As a result of studies made by the inventors of the present invention, it has been found that the number of m in the general formula (1) has influences on influx and efflux rates. Therefore, when evaluating an influence of a compound on a function of a transporter, the number of m can be suitably adjusted depending on power of influence of the compound. Specifically, when the evaluation probe for CNS permeability of the present invention includes a compound of which the number of m is 1, the probe can be particularly strongly transported by a transporter, and hence such probe can be used for evaluating a compound that is strongly effective to a transporter. When the evaluation probe for CNS permeability of the present invention includes a compound of which the number of m is 2, the probe is rather slowly transported by a transporter, and hence such probe can be used for evaluating a compound that is weakly effective to a transporter.

The dye compound represented by the general formula (1) according to the present invention is commercially available. Alternatively, the dye compound may be synthesized by a known method.

Preferred specific examples of the dye compound represented by the general formula (1) (compound (I) to compound (46)) are given below. However, the present invention is by no means limited to the following examples.

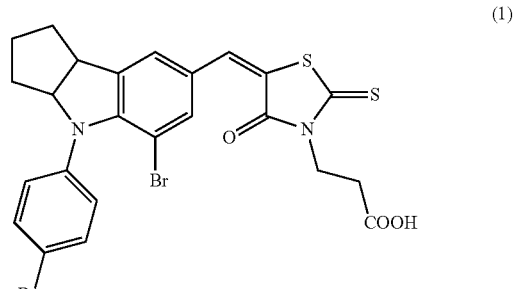

(1)

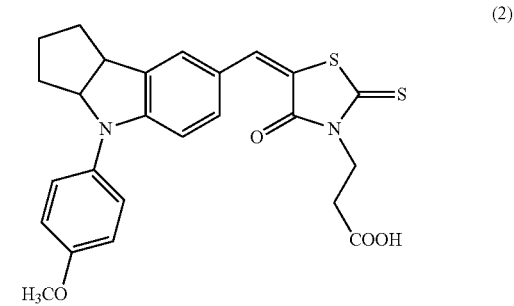

(2)

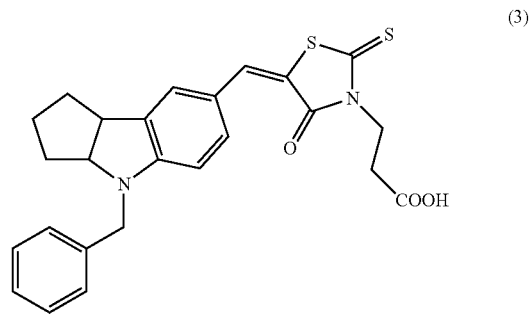

(3)

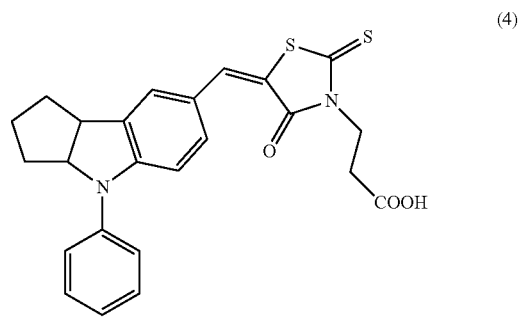

(4)

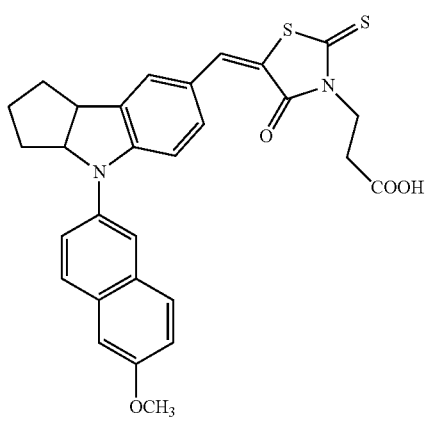
(5)
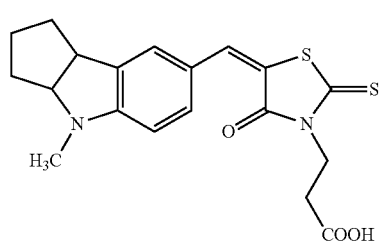
(6)
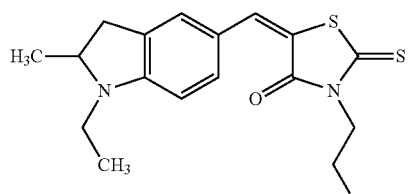
(7)
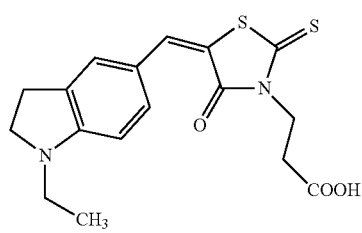
(8)
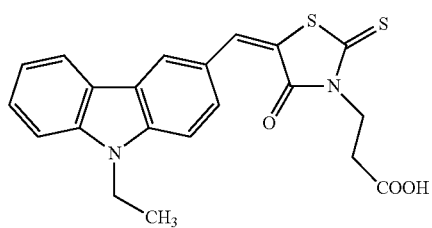
(9)
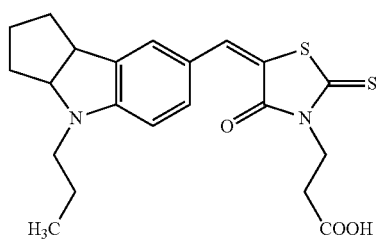
(10)
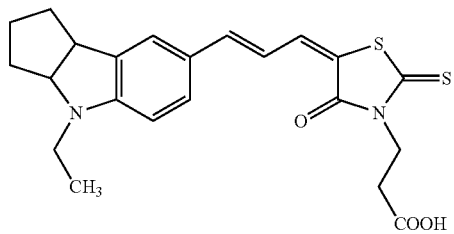
(11)
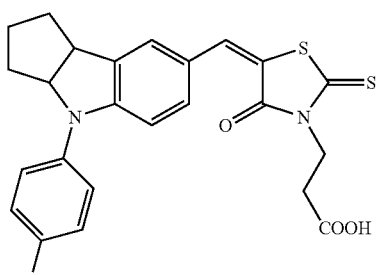
(12)
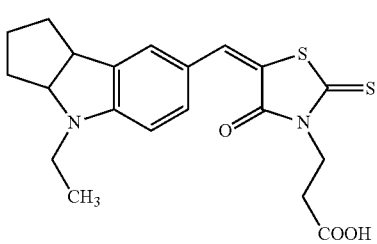
(13)
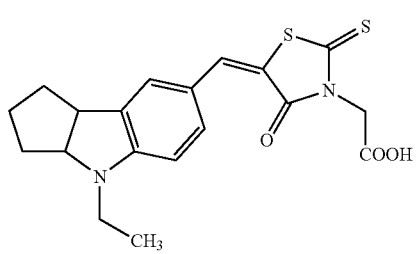
(14)
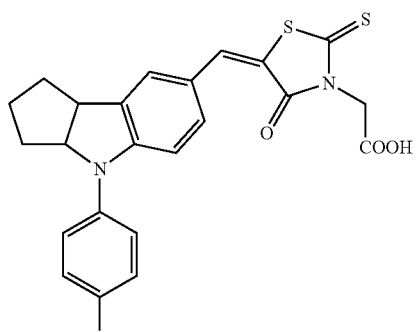
(15)
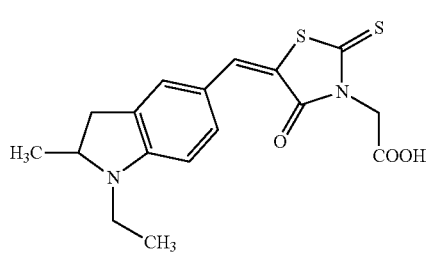
(16)

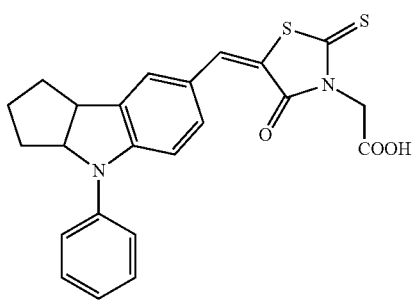
(17)
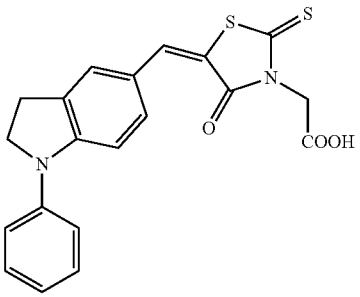
(22)
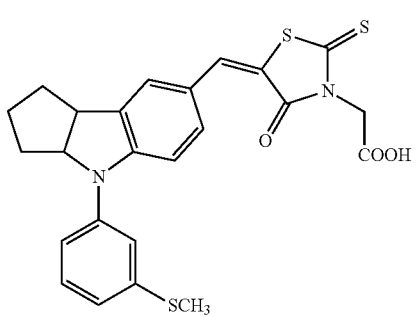
(18)
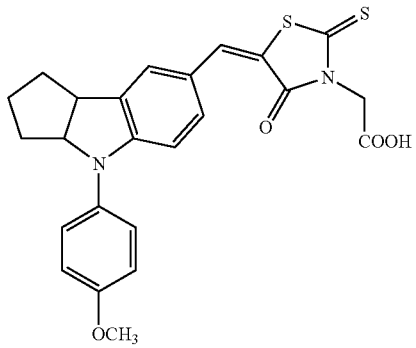
(23)
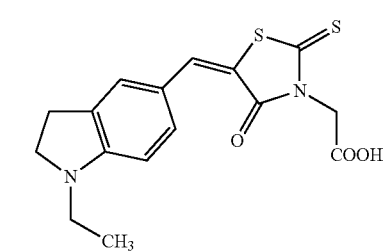
(19)
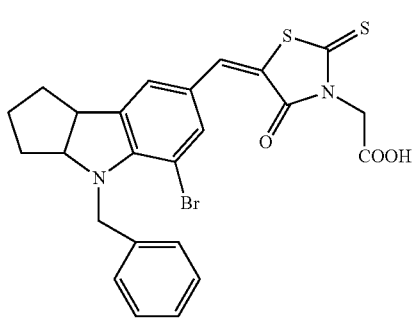
(24)
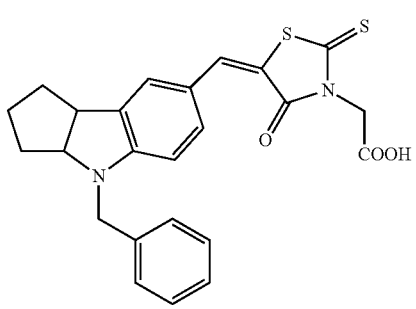
(20)
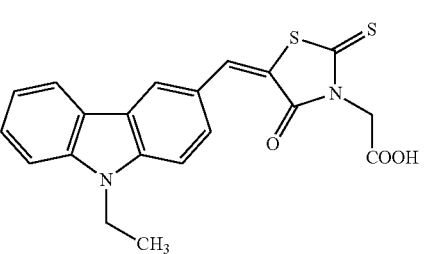
(25)
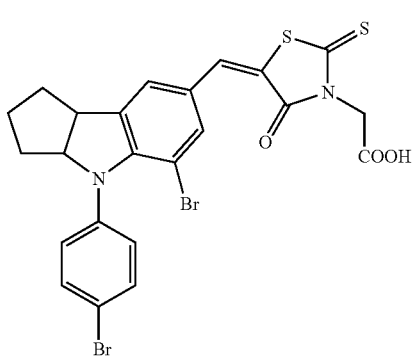
(21)
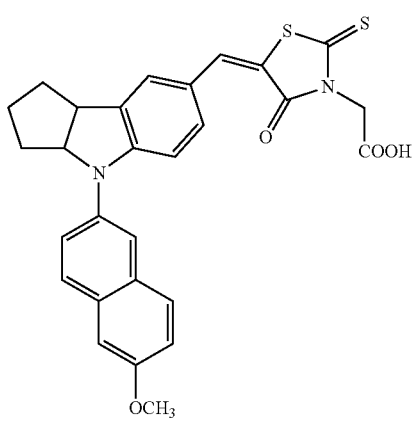
(26)

(27)
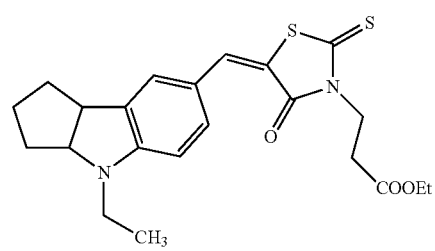
(28)
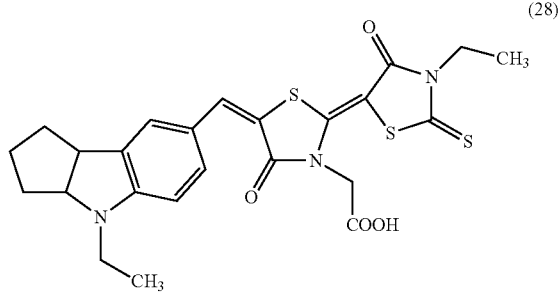
(29)
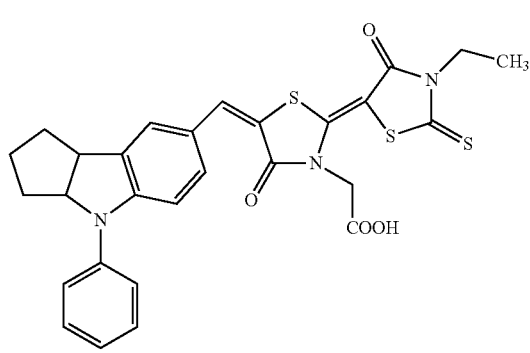
(30)
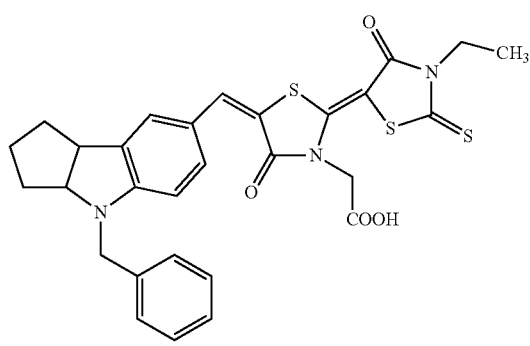
(31)
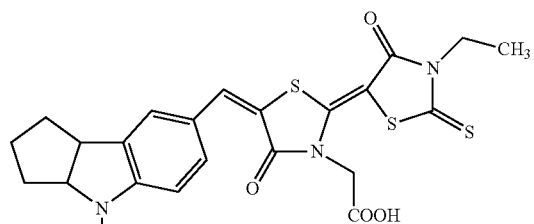
(32)
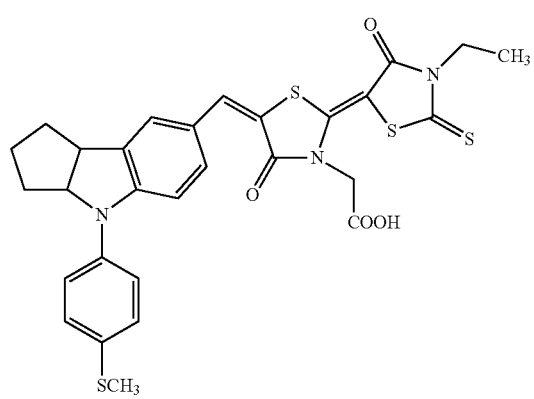
(33)
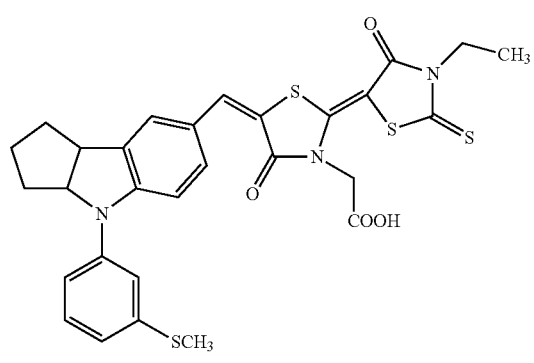

(34)
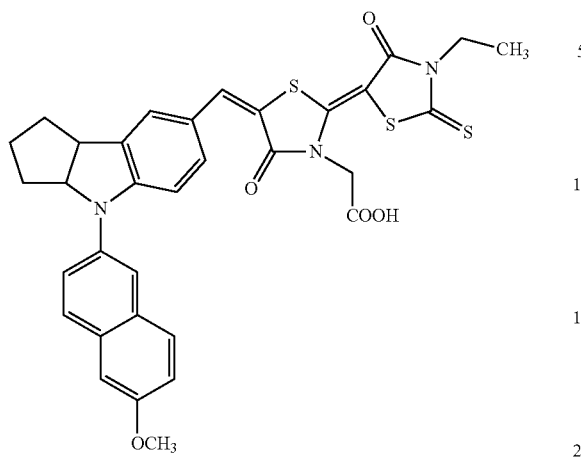
(35)
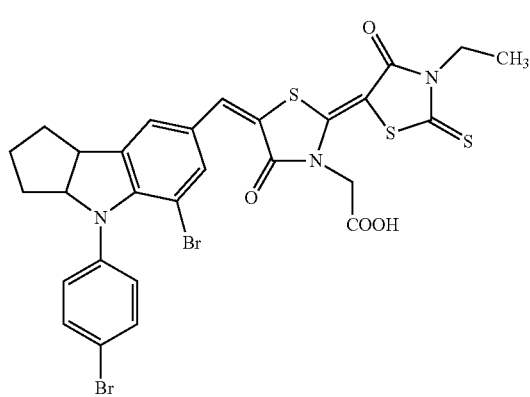
(36)
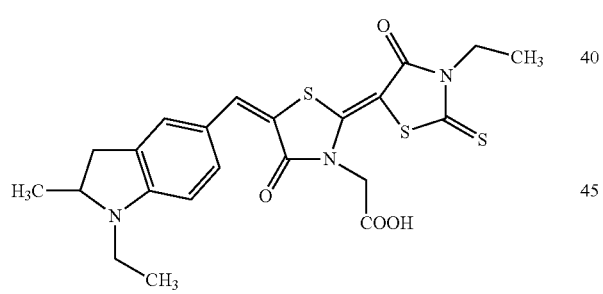
(37)
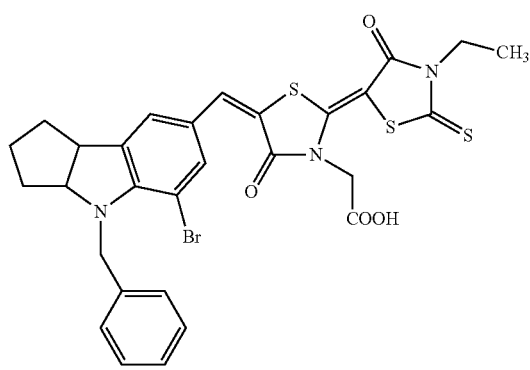
(38)
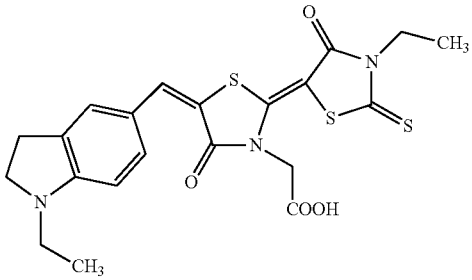
(39)
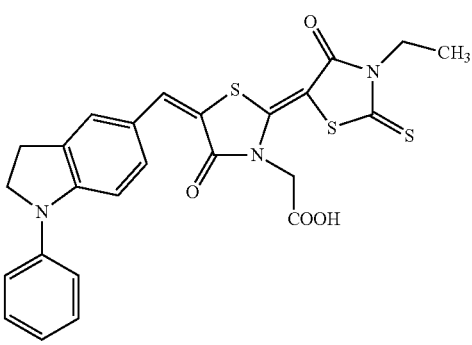
(40)
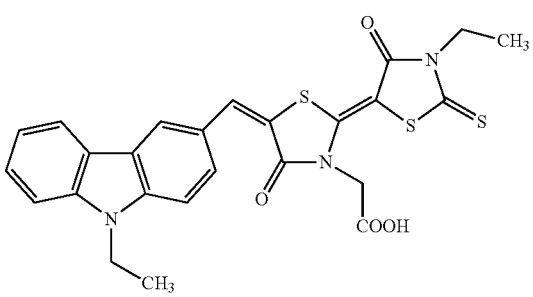
(41)
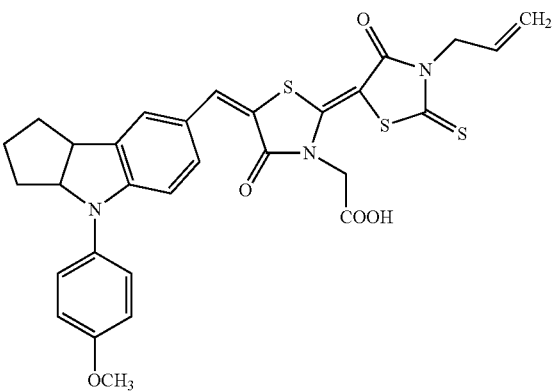

(Compounds)

As the compound represented by the general formula (1) included in the evaluation probe for CNS permeability of the present invention, a compound having a molecular weight of 300 or more to 1,000 or less is preferably selected, and a compound having a molecular weight of 300 or more to 650 or less is more preferably selected. Further, as a result of studies made by the inventors of the present invention, it has been found that the molecular weight of $R_1$ in the general formula (1) has influences on influx and efflux rates. In general evaluation, $R_1$ in the general formula (1) preferably has a molecular weight of 1 or more to 250 or less.

Further, the compound of the present invention is preferably a fluorescent compound having fluorescent property. The fluorescent compound, which has high sensitivity, can label and visualize a transporter at a low concentration, and hence the amount of the compound to be required can be relatively reduced. Further, the selection of a combination of compounds and the like having different fluorescence spectra depending on the kind of a transporter that serves as a substrate and on substrate specificity is highly useful because functions of multiple transporters can be evaluated by multiple labeling, leading to an increased amount of information obtained through one observation. The use of the compound of the present invention as the fluorescent compound as described above saves the trouble of labeling a substance to be tested. Hence, even screening of numerous target substances can be simply carried out.

The concentration of the compound included in the evaluation probe for CNS permeability of the present invention is not particularly limited and it can be appropriately regulated depending on a target site and a compound to be used. The compound is used at a concentration of generally 0.001 ng/mL or more to 100 µg/mL or less, more preferably 0.001 ng/mL or more to 10 µg/mL or less, more preferably 0.001 ng/mL or more to 5 µg/mL or less.

In the evaluation probe for CNS permeability of the present invention, at least one kind of compound represented by the general formula (1) is used by being dissolved in an appropriate solvent. The solvent is not particularly limited as long as it has no influence on a living body. However, an aqueous liquid having high biocompatibility is preferred. Specific examples thereof include: water; physiological saline; buffers such as phosphate-buffered saline (PBS) and Tris; alcohol-based solvents such as methanol, ethanol, isopropanol, butanol, ethylene glycol, and glycerin; organic solvents such as N,N-dimethylsulfoxide (hereinafter, abbreviated as "DMSO") and N,N-dimethylformamide (hereinafter, abbreviated as "DMF"); cell culture media such as Dulbecco's modified Eagle medium (D-MEM) and Hanks' balanced salt solutions (HBSS); and infusions such as lactated Ringer solutions. It is particularly preferred that 50% or more of water be included in those solvents. Further, a mixture of two or more kinds of those solvents may be used. Of those solvents, methanol, ethanol, or DMSO is particularly preferred.

A production method for the evaluation probe for CNS permeability of the present invention is not particularly limited, and the evaluation probe may be prepared, for example, by diluting a concentrated solution of the compound dissolved in the solvent as described above.

When the compound is low in water solubility, the compound may be used by being dissolved in an appropriate solvent and then diluted with purified water.

One kind of additive may be added alone or two or more kinds thereof may be added in combination to the evaluation probe for CNS permeability of the present invention when a salt concentration, a pH, and the like suitable for a living body need to be controlled.

The additive to be used in the present invention is not particularly limited as long as it has no influence on a CNS tissue-labeling composition, and examples thereof include humectants, surface tension adjusters, thickeners, salts such as sodium chloride, various pH adjusters, pH buffers, preservatives, antibacterial agents, sweetners, and flavors.

Each of the pH adjusters preferably adjusts a pH to 5 to 9, and examples thereof include, but not particularly limited to, hydrochloric acid, acetic acid, phosphoric acid, citric acid, malic acid, sodium hydroxide, and sodium bicarbonate.

The evaluation probe for CNS permeability of the present invention may also be used as a probe labeled with a radionuclide. The kind of the radionuclide to be used for labeling is not particularly limited and may be appropriately selected depending on usage. Specifically, in the case of measurement by PET, for example, positron-emitting nuclides such as $^{11}C$, $^{14}C$, $^{13}N$, $^{15}O$, $^{18}F$, $^{19}F$, $^{62}Cu$, $^{68}Ga$, and $^{78}Br$ may be used. Of those, preferred is $^{11}C$, $^{13}C$, $^{15}O$, or $^{18}F$, and particularly preferred is $^{11}C$ or $^{18}F$. Further, in the case of measurement by SPECT, for example, gamma-emitting nuclides such as $^{99m}Tc$, $^{111}In$, $^{67}Ga$, $^{201}Tl$, $^{123}I$, and $^{133}Xe$ may be used. Of those, preferred is $^{99m}Tc$, $^{123}I$. In the case of measuring an animal other than a human, radionuclides each having a long half-life, for example, such as $^{125}I$, may be used. In the case of measurement by GREI, for example, $^{131}I$, $^{85}Sr$ or $^{65}Zn$ may be used.

A CNS tissue-labeling composition labeled with a radionuclide may be used for, for example, imaging by autoradiography, positron emission tomography (PET) using a positron-emitting nuclide, single photon emission computed tomography (SPECT) using various gamma-emitting nuclides, or the like. Detection may be carried out by magnetic resonance imaging (MRI) utilizing an MR signal derived from a fluorine nucleus or $^{13}C$. Imaging may further be carried out using a compton camera (GREI) or the like, which allows simultaneous imaging of multiple molecules, as a next-generation molecular imaging apparatus. Still further, for example, the evaluation probe for CNS permeability may be quantified using a liquid scintillation counter, an X-ray film, an imaging plate, or the like.

The concentration of the evaluation probe for CNS permeability labeled with a radioisotope such as $^{14}C$ in blood (or urine or feces) may be measured by accelerator mass spectrometry (AMS) or the like to obtain pharmacokinetic information about an unchanged body or a metabolite of a labeled substance (e.g., an area under the blood drug concentration-time curve (AUC), a blood concentration half-life (T1/2), a maximum blood concentration (Cmax), a time-to-maximum blood concentration (Tmax), a distribution volume, a first-pass effect, a bioavailability, and excretion rates in feces and urine).

The radionuclide may be included in or bound to the compound represented by the general formula (1).

A method for labeling with the radionuclide is not particularly limited and may be a generally used method. Further, at least part of elements constructing the compound represented by the general formula (1) may be substituted by the radionuclide.

When the compound represented by the general formula (1) is labeled with the radionuclide, the compound preferably has a radioactivity of about 1 to 100 μCi per mM. In this case, the dosage of the evaluation probe for CNS permeability to be used is not particularly limited as long as there is no influence, and the dosage can appropriately be selected depending on the kind of a compound and the kind of a radionuclide used for labeling.

(Target)

Biological species whose influx and efflux of a substance through a CNS tissue can be evaluated using the evaluation probe for CNS permeability of the present invention are not particularly limited. Examples thereof include vertebrates including: bony fish such as *Takifugu rubripes*, *Takifugu niphobles*, *Tetraodon nigroviridis*, *Oryzias latipes*, and zebrafish; amphibians such as *Xenopus laevis*; birds such as *Gallus gallas domesticus* and *Coturnix japonica*; small animals such as rats, mice, and hamsters; large animals such as goats, pigs, dogs, cats, cattle, and horses; and primates such as monkeys, chimpanzees, and humans. In particular, according to the present invention, those individual organisms can be used and evaluated in a living state. Further, humans may be omitted from the biological species.

Of those biological specimens, it is preferred to use zebrafish. In recent years, in the USA and the UK, the zebrafish has been recognized as a third animal model following a mouse and a rat, and it has been elucidated that the zebrafish has 80% homology in full-genome sequence and almost the same number of genes, and it is very similar in development and structures of major organs and tissues as compared to a human. The zebrafish is particularly preferably used as an animal model for screening because a process in which the respective parts (organs such as heart, liver, kidney, and gastrointestinal tract) are differentiated and formed from fertilized embryos can be observed through a transparent body, which allows the inside of a living body to be observed in a non-invasive manner. In the zebrafish, claudin-5 and zonula occludens-1, major proteins constructing a tight junction in BBB, are expressed on 3 days post fertilization (dpf) (Brain Research Bulletin 75 (2008) 619-628). Major organs are formed on 6 to 7 dpf, and a P-glycoprotein responsible for substance efflux in BBB is also expressed on 8 dpf. Therefore, the zebrafish may be suitably used for evaluation of a CNS tissue. Further, the zebrafish has an advantage of being convenient for screening because about 200 or more fertilized embryos are obtained per spawning to provide zebrafish individuals having the same genetic background.

Blood-nerve barriers which can be evaluated using the evaluation probe for CNS permeability of the present invention are exemplified by a blood-brain barrier (BBB), a blood-cerebrospinal fluid barrier (BCSFB), and a blood-retinal barrier (BRB). Of those, a blood-brain barrier and a blood-cerebrospinal fluid barrier are preferably evaluated, and a blood-brain barrier is more preferably evaluated. In those blood-nerve barriers, influx and efflux transporters for a compound can be evaluated for their functions. In particular, an efflux transporter can be suitably evaluated for its function. An ABC transporter can be more preferably evaluated.

In the evaluation probe for CNS permeability of the present invention, permeation of a substance to the CNS tissue may or may not be observed when only the probe is administered. When only the probe is administered, permeability of a substance through the CNS tissue can be evaluated.

Further, even in the case where no permeation of a substance to the CNS tissue is observed when only the probe is administered, permeation to the CNS tissue is observed by allowing the probe to act simultaneously with a compound having an influence on a function of a transporter. As a result, a function of the substance having an influence on the function of the transporter in the CNS tissue can be evaluated. Similarly, in the case where permeation to the CNS tissue is observed even when only the probe is administered, a function of a substance having an influence on a function of a transporter can be evaluated based on disappearance of permeability to the CNS tissue or a change (increase or decrease) in rate of permeability to the CNS tissue by allowing the probe to act simultaneously with the compound having an influence on the function of the transporter. In the present invention, appearance or disappearance of permeability to the CNS tissue and a change in rate of permeability to the CNS tissue are collectively referred to as "varying permeability to the CNS tissue." As the compound of the present invention, there is particularly preferably used a compound which shows no or very low permeability to the CNS tissue when only the evaluation probe for CNS permeability is exposed, but which has varying permeability to the CNS tissue when the probe is exposed simultaneously with a substance having an influence on a function of a transporter.

The evaluation probe for CNS permeability of the present invention does not need to be administered to a living body by invasive means, and permeate into a living body through, for example, exposure to the living body, or oral administration or transmucosal administration. Thus, a transporter can be evaluated without causing any damage on a biological specimen. That is, the prove can be administered to a living individual organism without causing any surgical damage such as dissection of tissues in the vicinity of the CNS and damage of the CNS tissue or a nerve tissue connected to the CNS tissue caused by needlestick. It should be noted that the present invention is not intended to omit an administration method accompanied with surgical damage.

The administration method without causing any surgical damage is not particularly limited, and examples thereof include a method including exposing the evaluation probe for CNS permeability to part or whole of an individual organism, a method including oral contact, a method including transpulmonary (or transbranchial) contact, a method including transnasal contact, a method including transgastrointestinal contact, a method including transmucosal contact, a method including transfluid contact, a method including sublingual contact, a method including intravascular contact such as intravenous contact or intraarterial contact, a method including intraperitoneal contact, an injection method such as intravaginal, subcutaneous, intradermal, intravesical, or intrabronchial injection, and a method including contact into a living body by means such as spraying or application. In the case of administration to an animal, the administration mode, administration route, and dosage are appropriately selected depending on the body weight and condition of an animal of interest.

The compound included in the evaluation probe for CNS permeability of the present invention serves as a substrate for at least one kind of transporter constructing a barrier present in the CNS tissue. Examples of the transporter include, but not particularly limited to, an ABC transporter, an SLC transporter, a glucose transporter, and a dopamine transporter. The compound serves as a substrate for preferably an efflux transporter, more preferably an ABC transporter, still more preferably Pgp, a breast cancer resistance protein (BCRP), or multidrug resistance-associated proteins (MRPs) 1 to 8.

The phrase "serve(s) as a substrate for a transporter" as used herein refers to being capable of being selectively transported by an influx transporter, or being incapable of being transported in the presence of an influx transporter inhibitor or having varying permeability via the transporter in the presence of an influx transporter inhibitor. Alternatively, the phrase "serve(s) as a substrate for a transporter" as used herein refers to being selectively transported by an efflux transporter, being transported by an efflux transporter in the absence of an efflux transporter inhibitor but being not transported in the presence of the inhibitor, or having varying permeability via an efflux transporter in the presence of an efflux transporter inhibitor.

Through the use of the evaluation probe for CNS permeability of the present invention, functional evaluation of a transporter can be carried out in a stained state in, for example, CNS tissues constructed of cerebrum (telencephalon), cerebral cortex, basal ganglion, mesencephalon, cerebellum, diencephalon, hindbrain (mantle), pons, medulla oblongata, spinal cord, optic tract, superior colliculus (optic tecta), pituitary gland, tectospinal (tectobulbar) tract, reticular formation, septal nucleus, amygdala, internal capsule, optic nerve, and like, cranial nerves such as optic nerve, those listed tissues under disease conditions, or neoplastic tissues or cancer tissues due to diseases. Further, when CNS tissues different from the foregoing are present depending on, for example, biological species, developmental stages, or developmental abnormality or diseases, those tissues can also be encompassed. By use of the evaluation probe for CNS permeability permeability of the present invention, functional evaluation of a transporter can be particularly preferably carried out based on staining property of optic nerve, optic tract, superior colliculus (optic tecta), pituitary gland, tectospinal (tectobulbar) tract, or reticular formation.

Cells included in the CNS tissue are not particularly limited, and examples thereof include nerve cells, oligodendrocytes, Schwann cells, Purkinje cells, amacrine cells, retinal ganglion cells, pyramidal cells, stellate cells, granule cells, glial cells, and tumor cells thereof or undifferentiated cells (stem cells) thereof.

(Evaluation Method)

An evaluation method for permeability of a substance through a CNS tissue using an evaluation probe for CNS permeability according to a second embodiment of the present invention includes: administering, to a biological specimen, the evaluation probe for CNS permeability of the present invention as a fluorescent compound by any method; after a lapse of a predetermined time, irradiating an observation site with light at an excitation wavelength to generate fluorescence having a longer wavelength; and observing the fluorescence to form an image. In addition, as necessary, the fluorescence is observed multiple times with time, and a change in observed value is followed up. In this case, in the same manner as in the first embodiment, only the probe may be administered, or a case where the probe and the compound having an influence on a function of a transporter are simultaneously administered may be compared to a case where only the probe may be administered.

The evaluation method of the present invention may be carried out in vivo, in vitro, or ex vivo.

The evaluation method of the present invention is not particularly limited as long as the method has no influence on the CNS tissue, it can be a method of capturing a condition and a change of the biological specimen as an image. Examples thereof include visible light imaging, near-infrared light imaging, and infrared light imaging, each of which involves irradiating the CNS tissue with one of visible light, near-infrared light, and infrared light, and observing with a camera, CCD, and the like; laser microscopy; fluorescent imaging, fluorescent microscopy, fluorescent endomicroscopy, confocal fluorescent microscopy, multiphoton-excited fluorescence microscopy, and narrow band imaging, each of which involves observing fluorescence derived from a biological specimen emitting light with a fluorescence endoscope etc. by irradiating the biological specimen with excitation light from an excitation light source; optical coherence tomography (OCT); and soft X-ray microscopy.

The wavelength for excitation to be used in the present invention is not particularly limited, varies depending on a dye compound represented by the general formula (1) to be used, and is not particularly limited as long as the dye compound represented by the general formula (1) of the present invention efficiently fluoresces. The wavelength is generally 200 to 1,010 nm, preferably 400 to 900 nm, more preferably 480 to 800 nm. In the case of using light in a near-infrared area, the wavelength is generally 600 to 1,000 nm, and a wavelength of 680 to 900 nm, which is excellent in biological permeability, is preferably used.

A fluorescence excitation light source to be used in the present invention is not particularly limited, and various laser light sources may be used. Examples of those laser light sources include a dye laser light source, a semiconductor laser light source, an ion laser light source, a fiber laser light source, a halogen lamp, a xenon lamp, and a tungsten lamp. Further, the use of various optical filters allows the acquisition of preferred excitation wavelengths and the detection of only fluorescence.

When an image of a CNS tissue is captured in such a condition that an individual organism has been irradiated with excitation light to cause light emission inside the CNS tissue as described above, a light emitting site can be easily detected. Further, a bright field image obtained by irradiation with visible light and a fluorescence image obtained by irradiation with excitation light can be combined by image processing means to observe the CNS tissue in more detail. Further, it is preferred to use a confocal microscope because an optical sectional image can be acquired.

A multiphoton-excited fluorescence microscope is preferably used for observing the inside of a tissue because of having high deep imaging capability and spatial resolution.

(Screening Method)

A screening method according to a third embodiment of the present invention includes detecting a compound acting on a CNS tissue in vivo using an evaluation probe for CNS permeability. The evaluation probe for CNS permeability of the present invention can screen the CNS tissue permeability and pharmacological action of a compound to be screened by using an individual organism such as zebrafish as a small bony fish in a living state, i.e., in vivo, and using permeability to a CNS tissue as an indicator. Through the use of zebrafish or the like as a living individual organism, the safety of the compound to be screened can also be simultaneously screened. In this regard, however, the present invention is not limited thereto, and for example, screening may be carried out in vitro or ex vivo.

The phrase "detect(ing) a compound acting on a CNS tissue" refers to detecting the presence or absence or characteristics of the compound acting on a CNS tissue by measuring a change in labeling property of the evaluation probe for CNS permeability of the present invention when a substance to be tested as a candidate for a substance having an influence on permeability of a substance through the CNS tissue (compound to be screened) is allowed to act on the CNS tissue. Specifically, as one example, a case where the compound to be screened and the evaluation probe for CNS permeability of the present invention are brought into contact with zebrafish is compared with a case where only the evaluation probe for CNS permeability of the present invention is brought into contact with zebrafish. Thus, screening can be carried out by observing an influence of the presence of the compound to be screened on a stained state of the CNS tissue with the evaluation probe for CNS permeability.

A method of bringing the compound to be screened into contact is not particularly limited. When the compound to be screened is water-soluble, there is given a method including administering the compound to be screened in feeding water. When the compound to be screened is not water-soluble, there is given a method including administering the compound to be screened alone dispersed in feeding water, or a method including administering the compound to be screened together with a trace amount of a surfactant and DMSO, a method including orally administering a mixture of the compound to be screened with a feed for an individual organism, or a method including parenterally administrating the compound to be screened by injection or the like. Of those, a method including administering the compound to be screened in feeding water is preferred because it can be easily carried out.

Through the use of at least one kind of evaluation probe for CNS parenterally of the present invention as an active ingredient, an effect, a side effect, or safety of the compound to be screened on the CNS tissue, and an influence thereof on a living organism can be screened using an individual organism. The evaluation probe for CNS parenterally to be used may be appropriately selected depending on target sites, purposes, inspection means, and the like. In addition, applications such as development of highly accurate diagnosis and treatment of a disease based on an influence on permeability of the evaluation probe for CNS permeability are expected.

The compound to be screened means a generic term for compounds having chemical actions, and examples thereof include, but not particularly limited to, a pharmaceutical agent, an organic compound, a therapeutic agent, an investigational drug, an agricultural chemical, a cosmetic, an environmental pollutant, and an endocrine disruptor.

A small bony fish may be preferably used in the screening method according to the present invention. Examples of the small bony fish to be used in the screening method according to the present invention include, but not particularly limited to, zebrafish, pufferfish, goldfish, *Oryzias latipes*, and *Giant rerio*. The small bony fish is preferred because it is very excellent in growth speed and cost as compared to a mouse, a rat, and the like. In particular, zebrafish is preferred because its genome has been almost completely decoded, its breeding and propagation are easy and thus it is available at a low price, and basic structures of major organs and tissues are completely formed 48 to 72 hours after fertilization.

The zebrafish is not limited to a wild-type zebrafish, and various disease-related zebrafish models may be used depending on purposes of screening. When the disease-related zebrafish models are used, an effect of a new drug candidate compound is found by observation, and the finding can be applied to screening of a therapeutic drug for a disease or a preventive drug for a disease.

EXAMPLES

Hereinafter, the present invention is described in more detail by way of examples. However, those examples are specific examples given for further comprehensive understanding of the present invention, and the present invention is by no means limited to those specific examples. It should be noted that "%" is on a mass basis unless otherwise stated. It should be noted that an $^1$H-NMR spectrophotometer (ECA-400, manufactured by JEOL Ltd.), LC/TOF MS (LC/MSD TOF, manufactured by Agilent Technologies, Inc.), and a spectral scanning multimode reader (Varioskan Flash, manufactured by Thermo Fisher Scientific Inc.) were used as analysis apparatuses.

Dye compounds represented by the general formulae (1) to (46) according to the present invention are commercially available. Alternatively, the dye compounds may also be synthesized by a known method.

Synthesis Examples of Compounds

Synthesis Examples 1 and 2 are described as typical synthesis examples of compounds.

Synthesis Example 1

Synthesis of Dye Compound (4)

To a solution of 3.0 g (11.4 mmol) of an aldehyde derivative (1) in 20 mL of acetic acid were added 2.2 g (11.5 mmol) of rhodanine-3-propionic acid and 0.9 g of ammonium acetate, followed by stirring under reflux for 2 hours. After completion of the reaction, 50 mL of water were slowly added dropwise thereto while cooling, and the mixture was cooled to room temperature. A solid precipitate was filtrated, washed twice with 100 mL of water, and further washed with 50 mL of 2-propanol, to afford 3.1 g (yield: 60.1%) of a target product (4).

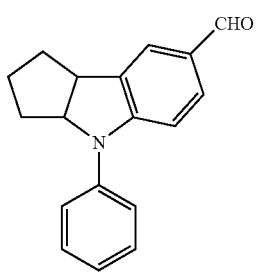

Aldehyde derivative (1)

Synthesis Example 2

Synthesis of Dye Compound (8)

To a solution of 1.75 g (10.0 mmol) of an aldehyde derivative (2) in 20 mL of toluene were added 1.13 g (10.0 mmol) of rhodanine-3-propionic acid and 2.5 g (30.0 mmol) of piperidine, followed by stirring under reflux for 2.5 hours. After completion of the reaction, the mixture was cooled to room temperature, diluted with 100 mL of toluene, supplemented with 100 mL of water, and stirred. After the whole had been left to stand still, an organic layer was separated and dried over anhydrous sodium sulfate. After filtration, toluene was distilled off under reduced pressure, and recrystallization of the residue from ethanol afforded 1.6 g (yield: 43.2%) of a target product (8).

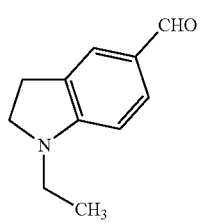

Aldehyde derivative (2)

Synthesis Examples of Other Dye Compounds

Other compounds shown in Table 1 below were synthesized by a method pursuant to Synthesis Example 1 or 2 above. Structures of those compounds were confirmed with the analysis apparatuses described above.

<Measurement of Fluorescence Characteristics of Dye Compounds>

5-µM solutions of Dye compounds 1 to 46 in DMSO were each prepared and measured for its excitation wavelength and fluorescence emission wavelength with an FL4500 fluorescence spectrometer manufactured by Hitachi High-Technologies Corporation.

TABLE 1

| Dye compound | Excitation wavelength $\lambda$ex | Fluorescence wavelength $\lambda$em |
|---|---|---|
| Compound 1 | 474 | 590 |
| Compound 2 | 521 | 634 |
| Compound 3 | 510 | 584 |
| Compound 4 | 502 | 604 |
| Compound 5 | 521 | 646 |
| Compound 6 | 517 | 590 |
| Compound 7 | 509 | 593 |
| Compound 8 | 510 | 597 |
| Compound 9 | 452 | 540 |
| Compound 10 | 519 | 592 |
| Compound 11 | 564 | 671 |
| Compound 12 | 518 | 647 |
| Compound 13 | 513 | 587 |
| Compound 14 | 507 | 585 |
| Compound 15 | 517 | 638 |
| Compound 16 | 510 | 590 |
| Compound 17 | 508 | 604 |
| Compound 18 | 509 | 604 |
| Compound 19 | 511 | 594 |
| Compound 20 | 506 | 581 |
| Compound 21 | 476 | 580 |
| Compound 22 | 505 | 612 |
| Compound 23 | 518 | 637 |

TABLE 1-continued

| Dye compound | Excitation wavelength λex | Fluorescence wavelength λem |
|---|---|---|
| Compound 24 | 486 | 578 |
| Compound 25 | 453 | 536 |
| Compound 26 | 525 | 646 |
| Compound 27 | 518 | 590 |
| Compound 28 | 545 | 637 |
| Compound 29 | 525 | 610 |
| Compound 30 | 546 | 631 |
| Compound 31 | 550 | 650 |
| Compound 32 | 544 | 658 |
| Compound 33 | 536 | 632 |
| Compound 34 | 543 | 649 |
| Compound 35 | 520 | 617 |
| Compound 36 | 541 | 640 |
| Compound 37 | 525 | 616 |
| Compound 38 | 541 | 642 |
| Compound 39 | 536 | 640 |
| Compound 40 | 494 | 551 |
| Compound 41 | 515 | 624 |
| Compound 42 | 543 | 636 |
| Compound 43 | 552 | 668 |
| Compound 44 | 548 | 656 |
| Compound 45 | 513 | 589 |
| Compound 46 | 516 | 585 |

[Evaluation of Substance Having Influence on Permeability of Substance to CNS Tissue Using Evaluation Probe for CNS Permeability]

Example 1

Figure 2:
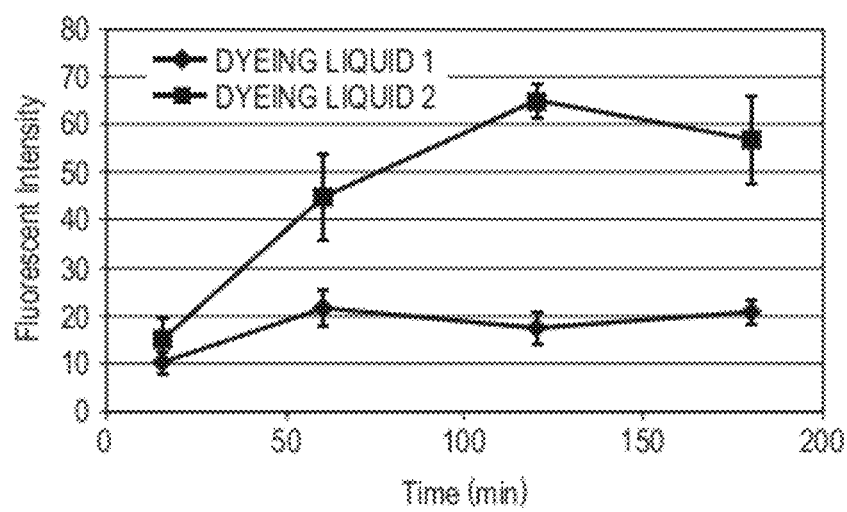
FIG. 2 shows a graph obtained by quantifying fluorescence intensities in the central nervous system tissues observed in Example 1.

Distilled water was added to a 1-mM solution of the compound (8) in DMSO to prepare a probe liquid 1 containing the compound (8) at a concentration of 1 μM. In addition, a probe liquid 2 containing the compound 8 as well as MK571, an ABC transporter inhibitor known to have inhibitory effects on MRP1, MRP2, MRP4, and the like, at 30 μM was prepared. 4 mL of the probe liquid 1 and each of 20 juvenile zebrafish on 7 days post fertilization were loaded into any well of a 6-well multiplate, and dye exposure was started. The zebrafish during dye exposure were each taken out of the well 15 minutes, 1 hour, 2 hours, and 3 hours after the starting of the dye exposure, and embedded in 3% methylcellulose on a slide glass to restrict its motion. Fluorescence images of CNS tissues were captured from the side surfaces of the zebrafish using a fluorescence stereo-microscope (MZ16FA manufactured by Leica), and fluorescence intensities of the respective samples were quantified using image analysis software Image J (NIH). FIG. 1 and FIG. 2 show the fluorescence images captured as described above and the fluorescence intensities quantified as described above, respectively. Further, a cranial nerve tissue and a retinal nerve tissue were observed using a confocal microscope (Pascal Exciter manufactured by Zeiss).

As a result, only the staining property of blood vessel was observed in the juvenile zebrafish to which the probe liquid 1 was exposed. On the other hand, the fluorescence intensities of the cranial nerve tissue and the retinal nerve tissue increased with time in the juvenile zebrafish to which the probe liquid 2 was exposed. This example demonstrated that the use of the evaluation probe for CNS permeability of the present invention allowed the evaluation of a compound having an inhibitory effect on an ABC transporter.

Example 2

A probe liquid 3 was obtained by changing the compound (8) used in the probe liquid 1 of Example 1 to the compound (13). Further, a probe liquid 4 and a probe liquid 5 were obtained by changing the compound (8) used in the probe liquid 2 to the compound (13), and adding digoxin, an organic anion transporter inhibitor, at 30 μM, as a transporter inhibitor, and adding fumitremorgin C (FTC), a breast cancer resistance protein (BCRP) inhibitor, at 10 μM, respectively, in place of MK571. Further, a washing liquid 1 (distilled water), a washing liquid 2 (solution containing 30 μM digoxin in distilled water), and a washing liquid 3 (solution containing 10 μM FTC in distilled water) were prepared as washing liquids for the dye exposed zebrafish.

Juvenile zebrafish on 7 days post fertilization were exposed for 1 hour by the same operation as in Example 1 except that the probe liquid 1 was changed to the probe liquid 3 and the probe liquid 2 was changed to the probe liquid 4 or the probe liquid 5. After that, the zebrafish were transferred to the washing liquids as shown in Table 2 and washed. The zebrafish were taken out of the wells immediately after the washing (60 minutes after the exposure), 1 hour after the washing (120 minutes after the exposure), and 2 hours after the washing (180 minutes after the exposure). In accordance with the same operation as in Example 1, fluorescence images of a cranial nerve tissue and a blood vessel on the zebrafish body side were captured and fluorescence intensities in the CNS tissue and the blood vessel were evaluated. Table 2 shows the evaluation results (++: strong fluorescence is found in the CNS tissue, +: weak fluorescence is found in the CNS tissue, −: substantially no fluorescence is found).

Figure 3:
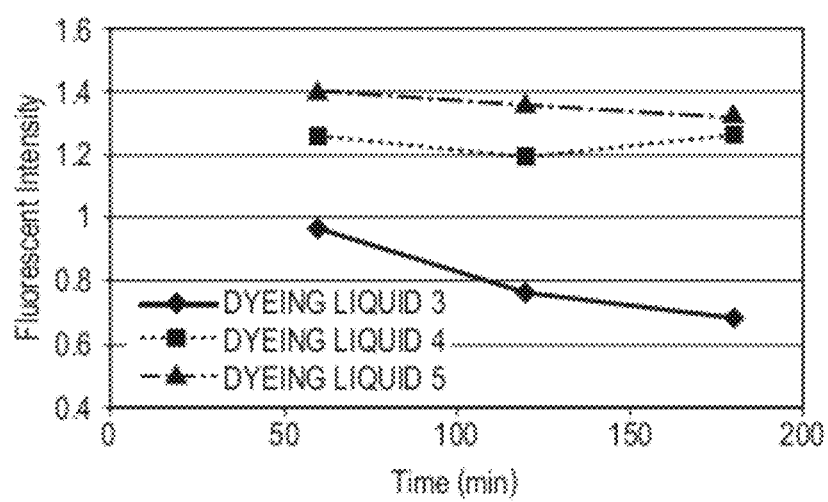
FIG. 3 shows a graph obtained by quantifying fluorescence intensities in central nervous system tissues observed in Example 2.

As a result, fluorescence was observed in the cranial nerve tissue after exposing for 60 minutes in all of the juvenile zebrafish to which the probe liquids 3 to 5 were exposed. However, the fluorescence intensities in the probe liquid 4 and the probe liquid 5 were higher than the fluorescence intensity in the probe liquid 3 (Table 2). Next, in order to examine an influence of substance transport from the CNS tissue, a ratio of the fluorescence intensity in the cranial nerve tissue with respect to the fluorescence intensity in the blood vessel was determined (FIG. 3). The results revealed that the relative fluorescence intensity decreased with time by washing in the zebrafish to which the probe liquid 3 free of a transporter inhibitor was exposed, whereas the relative fluorescence intensity was remarkably suppressed from decreasing in the zebrafish to which the probe liquid 4 and the probe liquid 5 each including a transporter inhibitor were exposed.

This example demonstrated that the use of the evaluation probe for CNS permeability of the present invention allowed the evaluation of compounds having inhibitory effects on an organic anion transporter and BCRP.

TABLE 2

| Exposure | Washing | Exposing for 60 minutes | Washing for 2 hours |
|---|---|---|---|
| probe liquid 3 | Washing liquid 1 | + | − |
| probe liquid 4 | Washing liquid 2 | ++ | + |
| probe liquid 5 | Washing liquid 3 | ++ | + |

Example 3

A probe liquid 6 was obtained by changing the compound (8) used in the probe liquid 1 of Example 1 to the compound (23). Further, a probe liquid 7 was obtained by adding MK571 and FTC, each at 30 μM, as a transporter inhibitor.

4 mL of the probe liquid 6 and 7 and each of 20 juvenile zebrafish on 7 days post fertilization were each loaded into any well of a 6-well multiplate, and exposure was started. The zebrafish during exposure were each taken out of the well 60 minutes, 180 minutes and 360 minutes after the starting of the exposure, and in accordance with the same operation as in Example 1, fluorescence images of a cranial nerve tissue and a blood vessel on the zebrafish body side were captured and fluorescence intensities in the CNS tissue and the blood vessel were evaluated.

Figure 4:
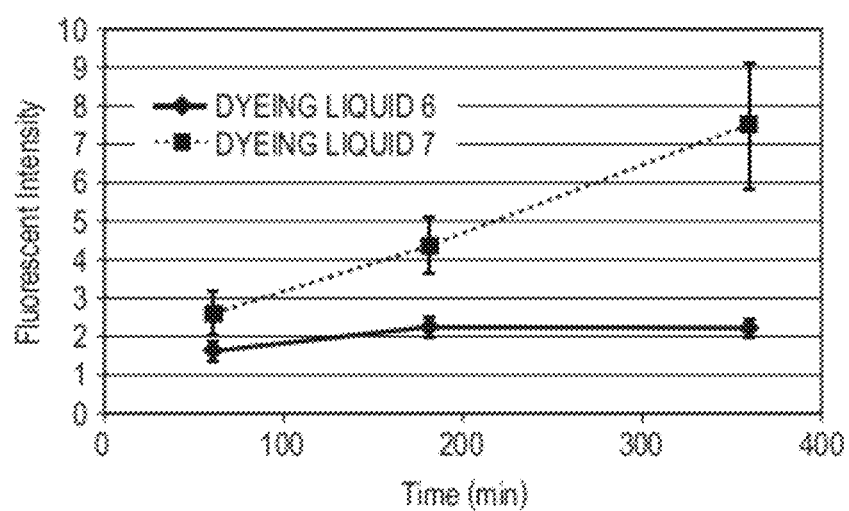
FIG. 4 shows a graph obtained by quantifying fluorescence intensities in central nervous system tissues observed in Example 3.

As a result, fluorescence was not observed in each of the 60 minutes, 180 minutes and 360 minutes exposure of the juvenile zebrafish to which the probe liquids 6 was exposed. However, the fluorescence intensities of the brain of the juvenile zebrafish to which the probe liquids 6 was exposed were increased over time (FIG. 4).

When adding MK571 and FTC, as a transporter inhibitor, was singly added at 30 μM, the increment of the fluorescence intensities of the brain of the juvenile zebrafish was not observed. The result suggests that the compound (23) was transported by both of MRP and BCRP. This result further suggests that, since the compound (23) has a characteristics of strongly transported by the transporters, the compound (23) is suitably for evaluating a compound that has a strong inhibition effect for a transporter, by using both of MK570 and FTC.

According to the present invention, it is possible to provide a technology capable of simply evaluating substance transport via a transporter by a less-invasive method in a system taken in consideration of an influence of a sophisticated biological mechanism such as an in vivo metabolism mechanism. The technology serves as a material useful in simply evaluating substance transport of a transporter. In discovery and development of drugs associated with diseases of the CNS including brain and retina, it is an important technical problem to enhance the delivery efficiency of a drug through the CNS tissue. Here, the use of the present invention allows permeation of a substance through the CNS tissue to be evaluated with time, and allows high-throughput and high-precision screening to be carried out at low cost, leading to development of novel diagnosis and treatment methods for diseases and drastic development of research on the CNS. Thus, the technology is a basic technology extremely effective from the industrial and practical standpoints as well.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2011-030778, filed Feb. 16, 2011, and No. 2011-187500, filed Aug. 30, 2011, which are hereby incorporated by reference herein in their entirety.

What is claimed is:

1. An evaluation method for an influence of a substance to be tested on permeability of a substance through a central nervous system tissue, the method comprising:
   a first step of administering, to a first biological specimen, an evaluation probe for central nervous system permeability in a non-invasive manner;
   independently of the first step, a second step of administering, to a second biological specimen, the evaluation probe and a substance to be tested in a non-invasive manner; and
   a third step of detecting and comparing permeability of the evaluation probes administered in the first step and in the second step through the central nervous system tissue of the first and second biological specimens,
   wherein the detecting comprises observing, more than once over time, a dyeing state of the evaluation probe at a cranial nerve tissue,
   wherein the evaluation probe is a probe for visualizing a function of a transporter associated with at least one of influx and efflux in a central nervous system, and
   wherein the evaluation probe comprises at least one compound selected from the group consisting of compounds (1), (5)-(23), (25)-(28), and (30)-(46):

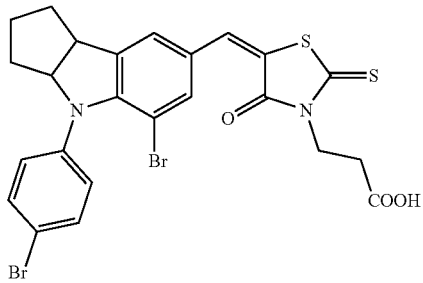

(1)

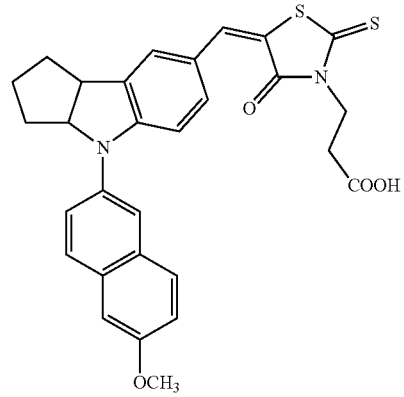

(5)

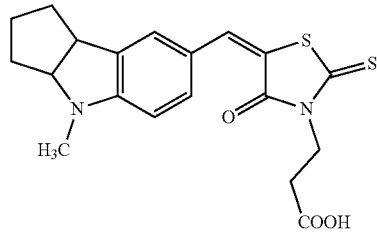

(6)

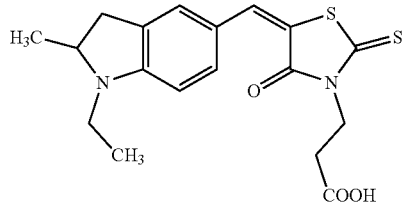

(7)

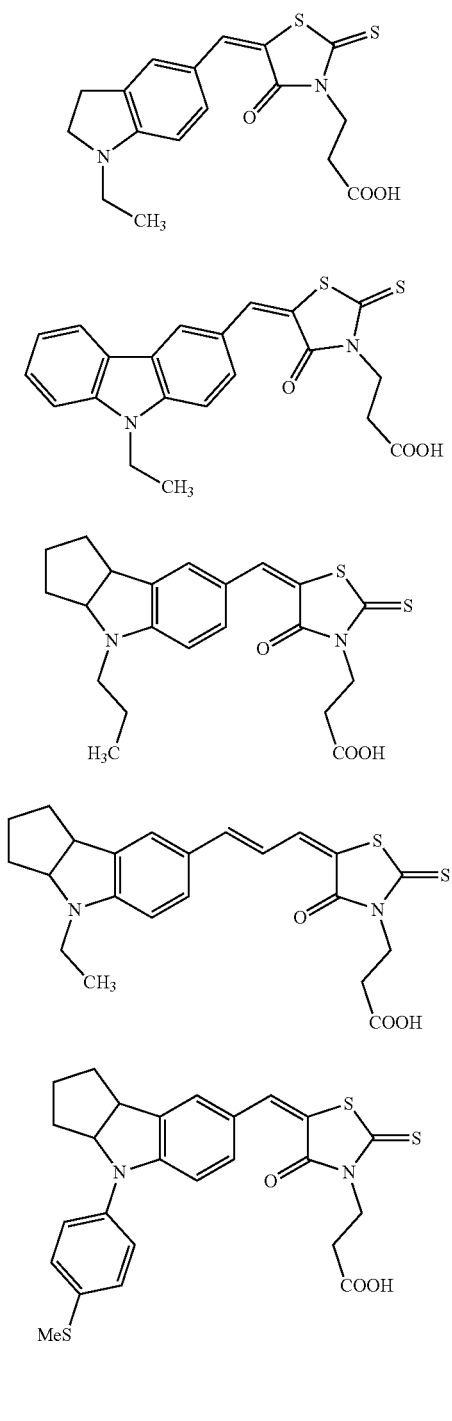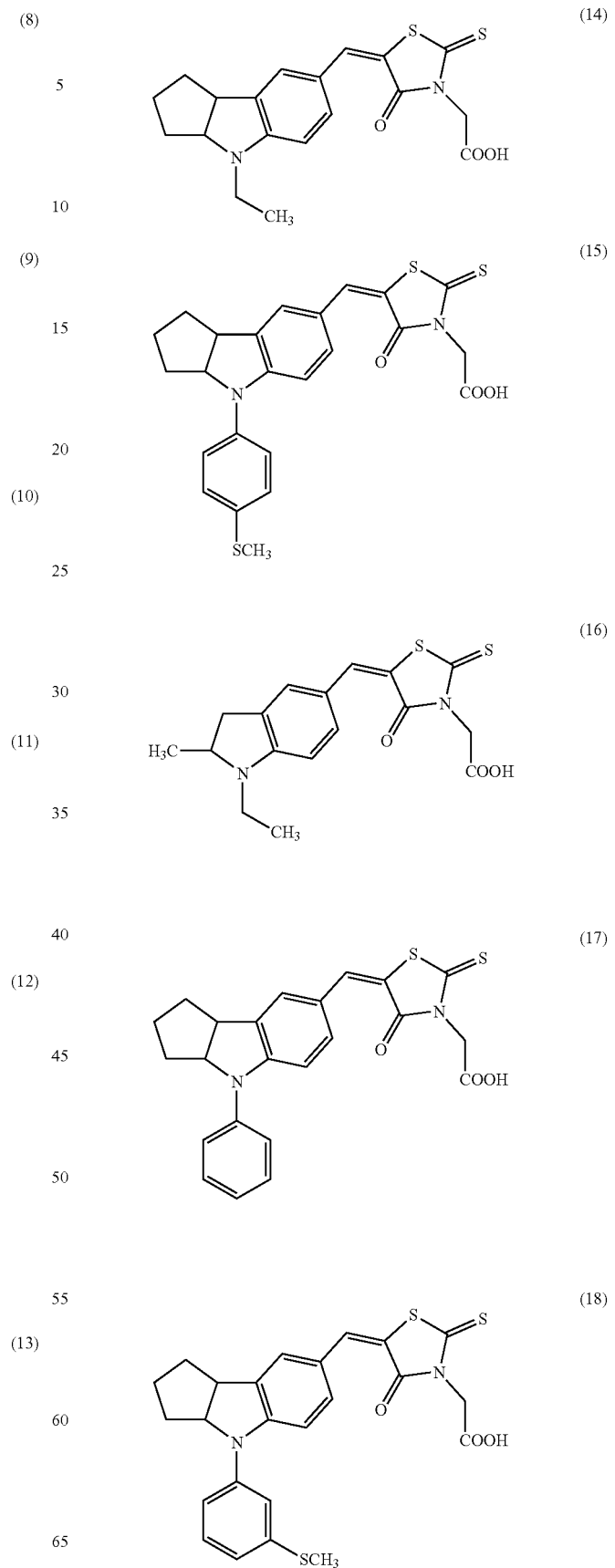

-continued
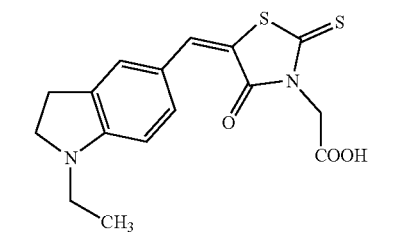
(19)
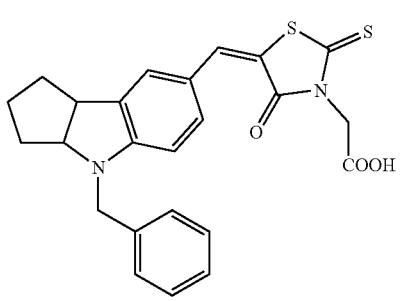
(20)
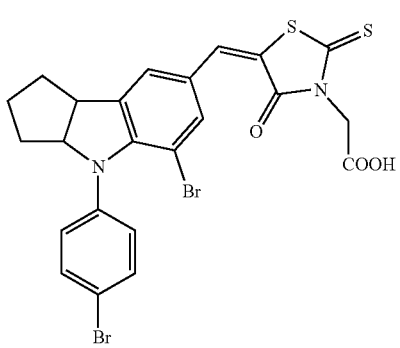
(21)
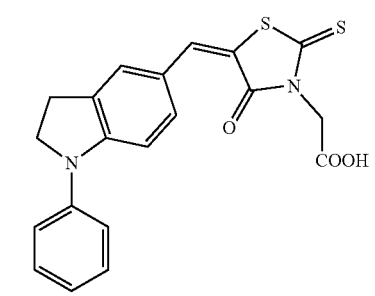
(22)
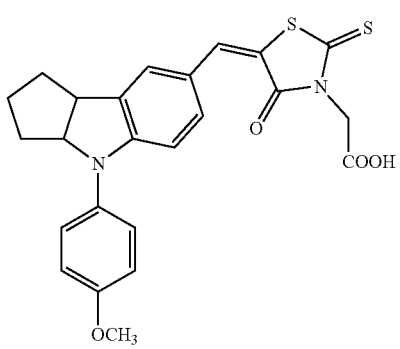
(23)
-continued
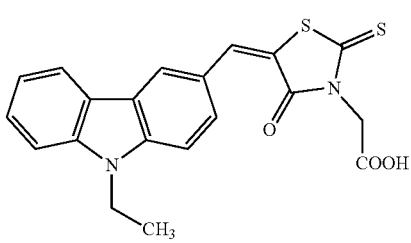
(25)
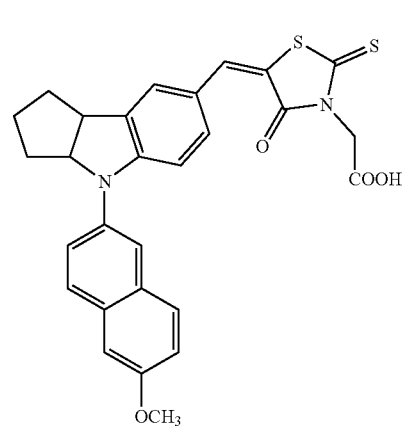
(26)
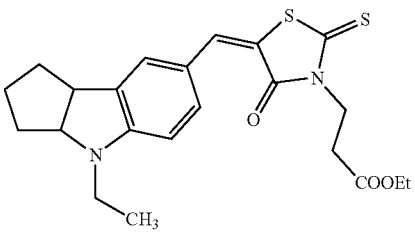
(27)
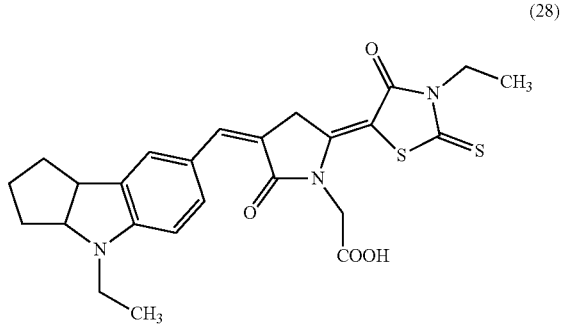
(28)
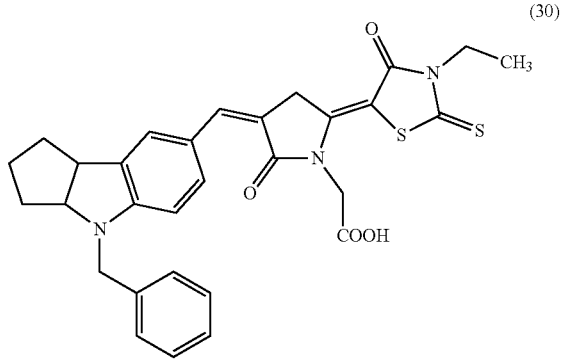
(30)

(31)
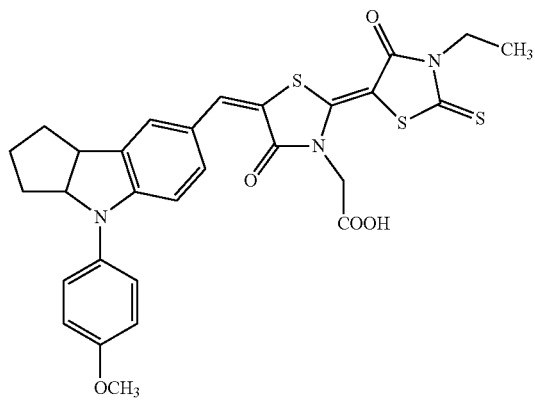
(32)
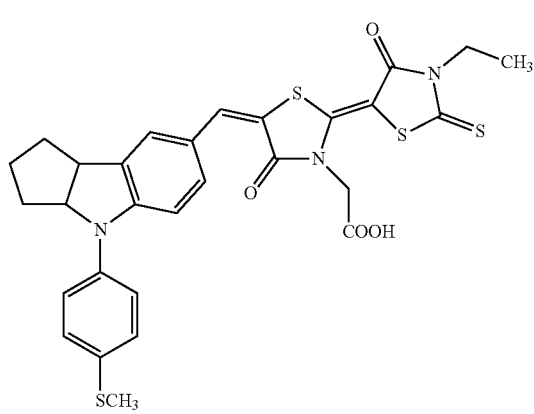
(33)
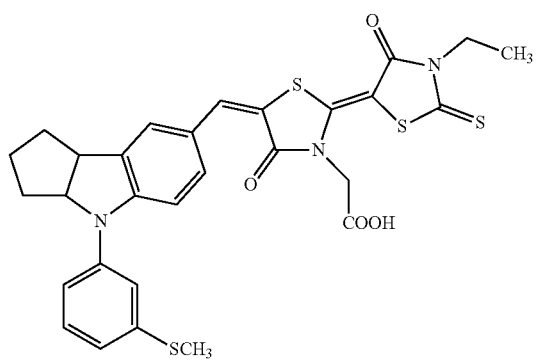
(34)
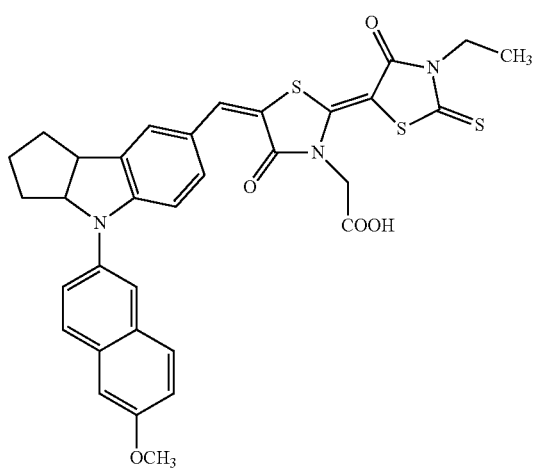
(35)
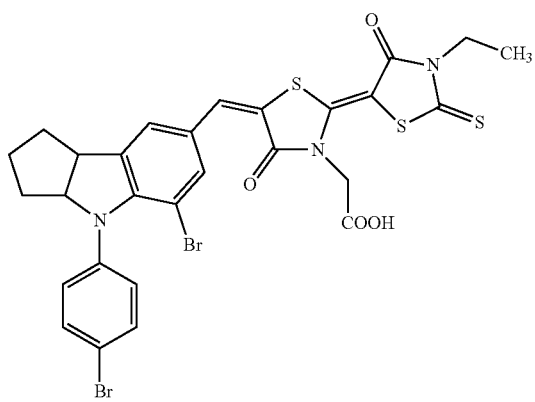
(36)
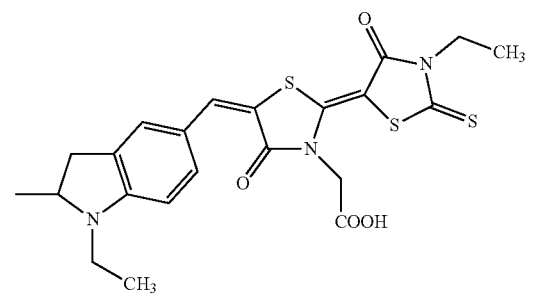
(37)
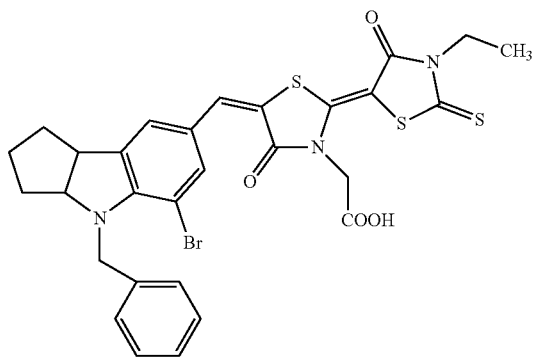

-continued
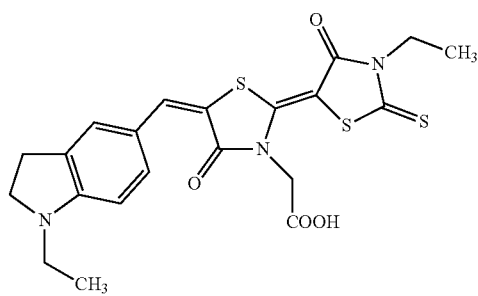
(38)
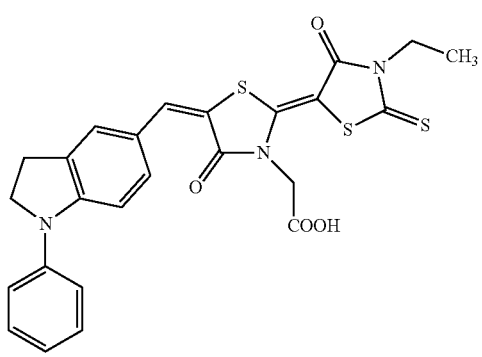
(39)
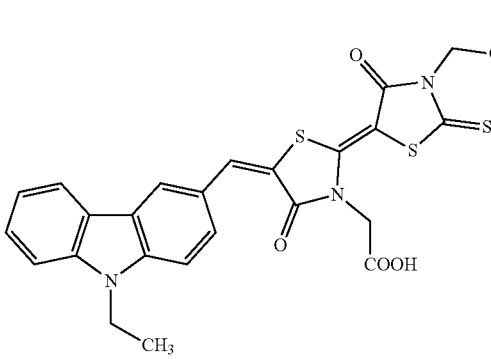
(40)
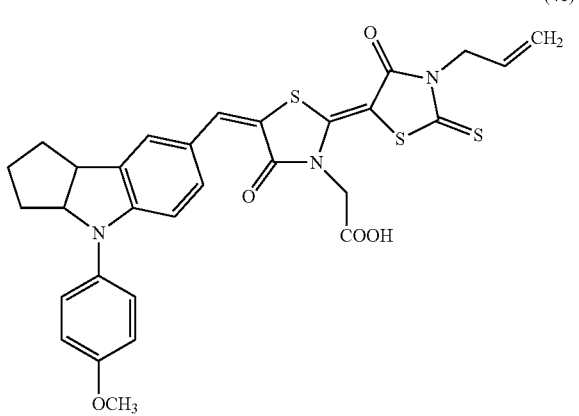
(41)
-continued
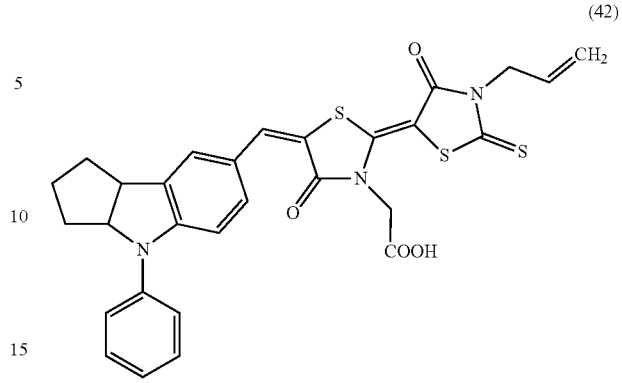
(42)
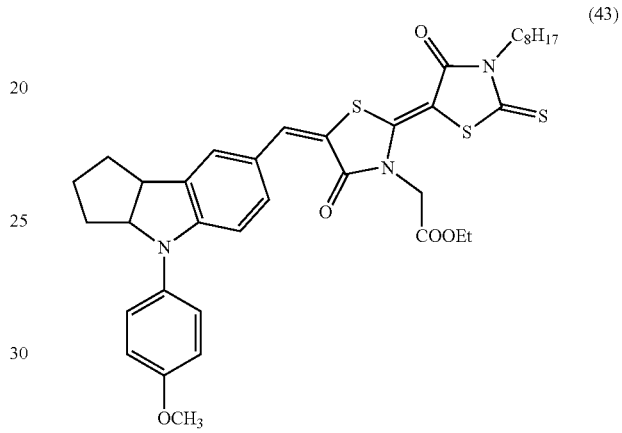
(43)
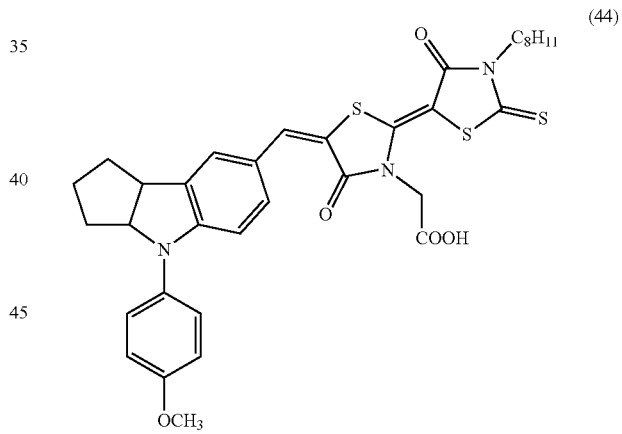
(44)
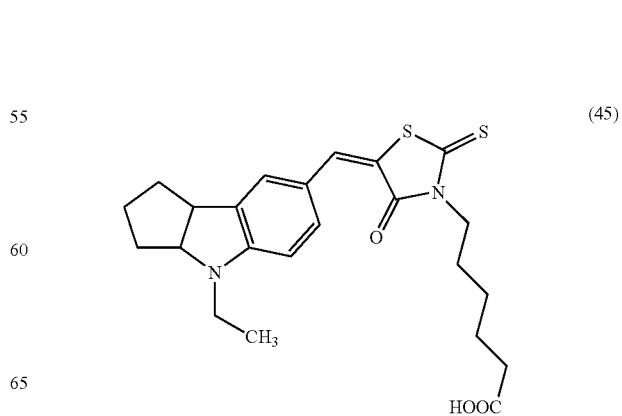
(45)

(46)

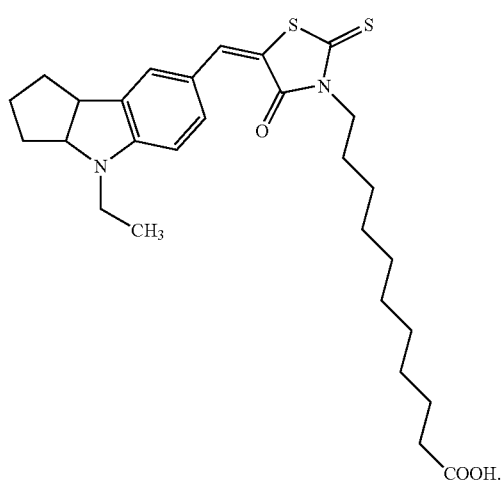

2. The method according to claim 1, wherein the transporter comprises one of an ABC transporter and an organic anion transporter.

3. The method according to claim 1, further comprising using a small bony fish comprising a zebrafish.

4. A screening method for a substance having an influence on permeability of a substance through a central nervous system tissue, the method comprising:
   a first step of administering, to a first biological specimen, an evaluation probe for central nervous system permeability in a non-invasive manner;
   independently of the first step, a second step of administering, to a second biological specimen, the evaluation probe and a substance to be tested, which serves as a candidate for the substance having the influence on permeability of the substance through the central nervous system tissue, in a non-invasive manner; and
   a third step of detecting and comparing permeability of the evaluation probes administered in the first step and in the second step through the central nervous system tissue of the first and second biological specimens,
   wherein the detecting comprises observing, more than once over time, a dyeing state of the evaluation probe at a cranial nerve tissue,
   wherein the evaluation probe is a probe for visualizing a function of a transporter associated with at least one of influx and efflux in a central nervous system, and
   wherein the evaluation probe comprises at least one compound selected from the group consisting of compounds (1), (5)-(23), (25)-(28), and (30)-(46):

(1)

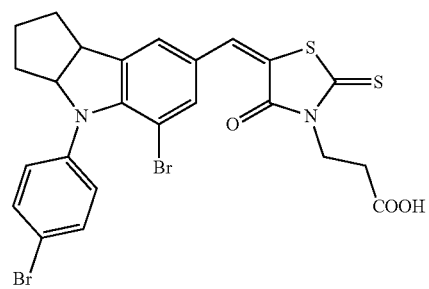

(5)

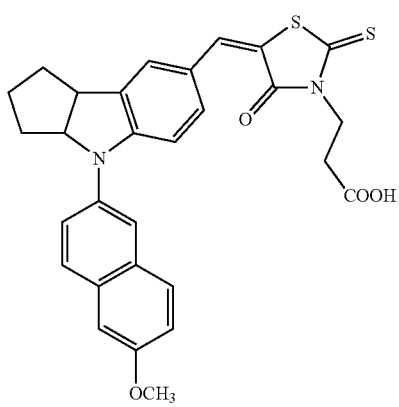

(6)

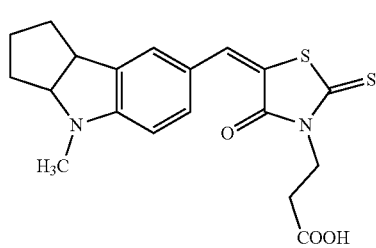

(7)

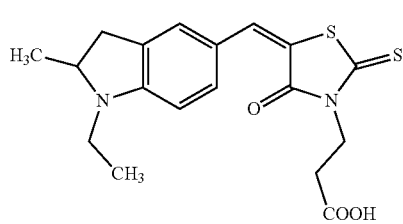

(8)

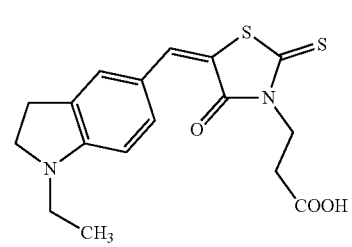

(9)

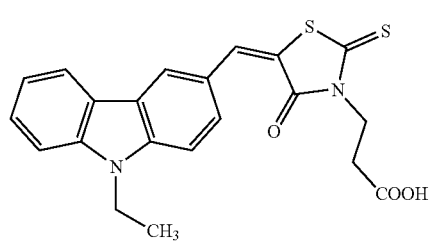

(10)

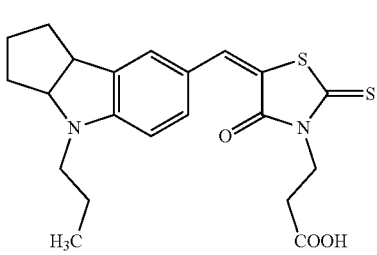

-continued
(11)
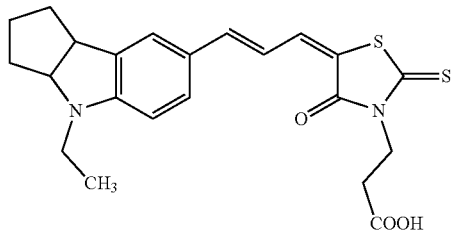
(12)
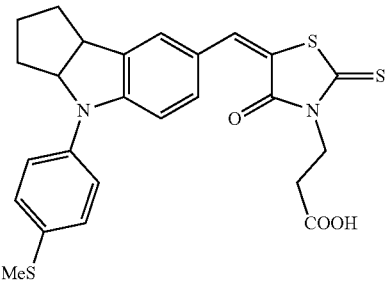
(13)
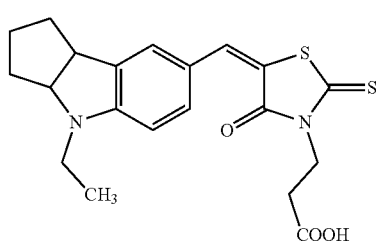
(14)
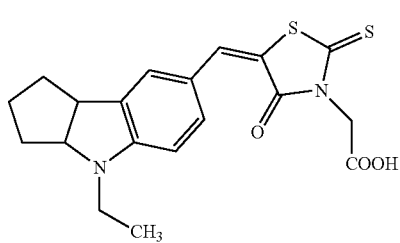
(15)
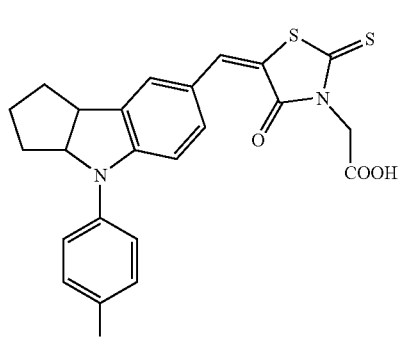
(16)
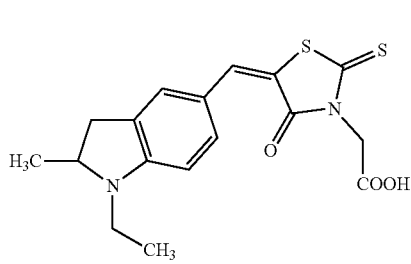
-continued
(17)
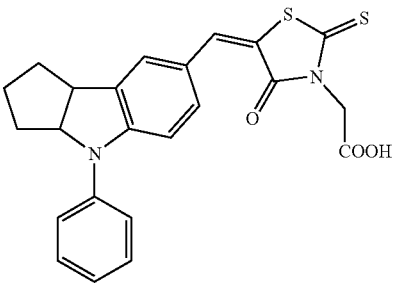
(18)
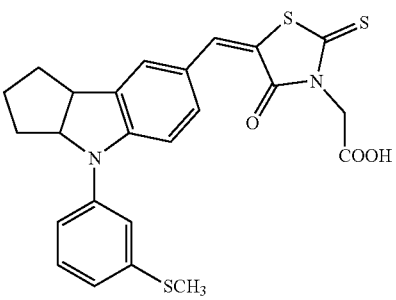
(19)
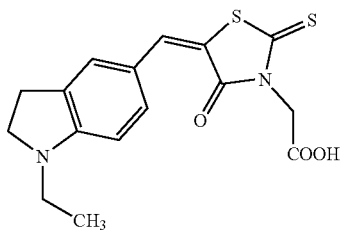
(20)
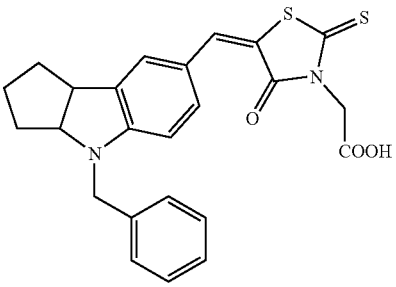
(21)
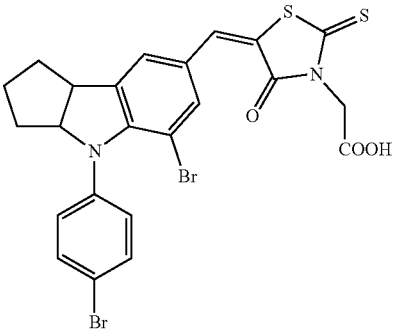

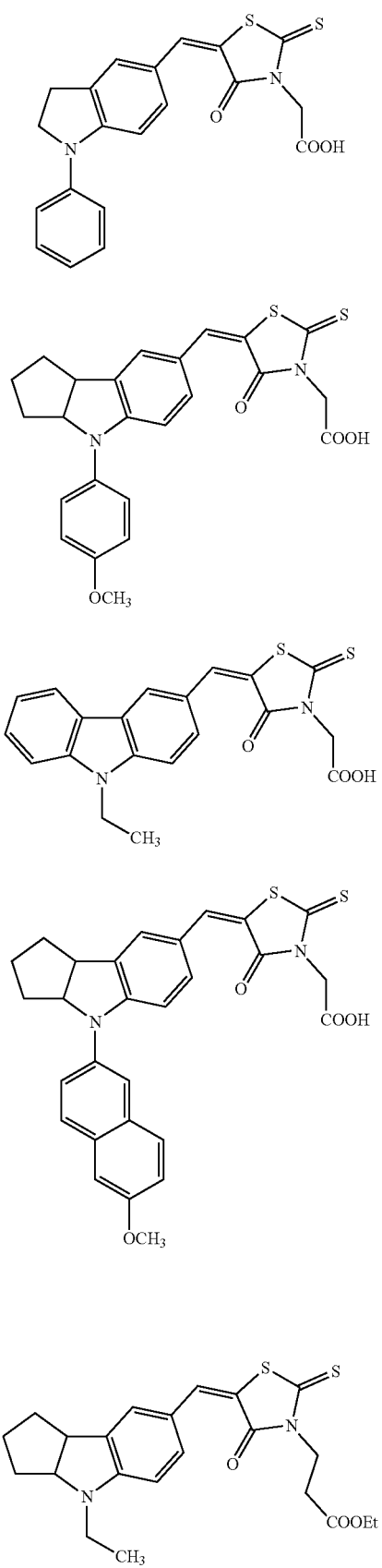

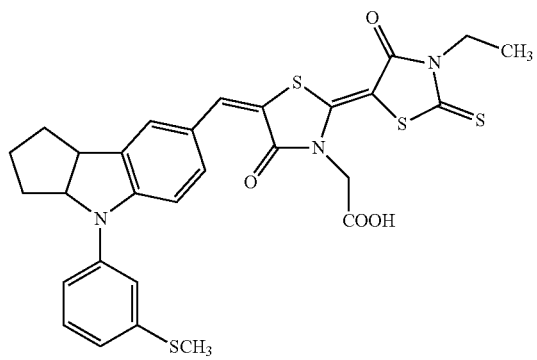
(33)
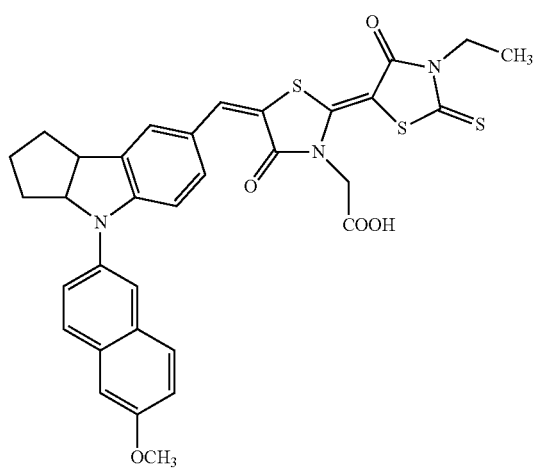
(34)
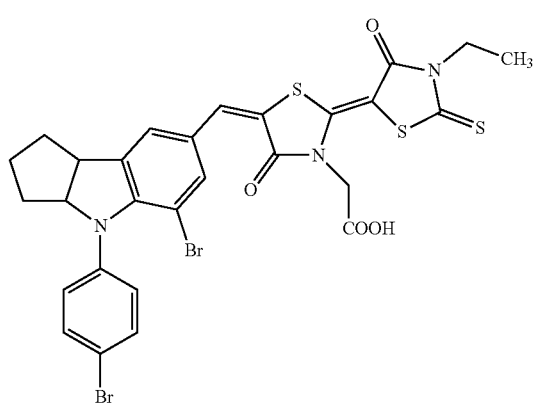
(35)
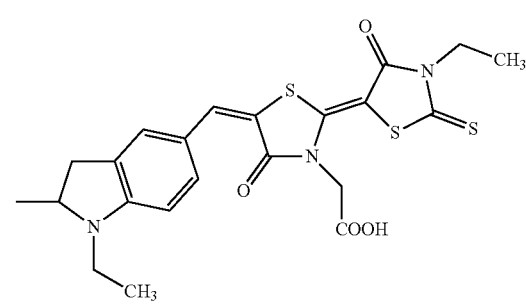
(36)
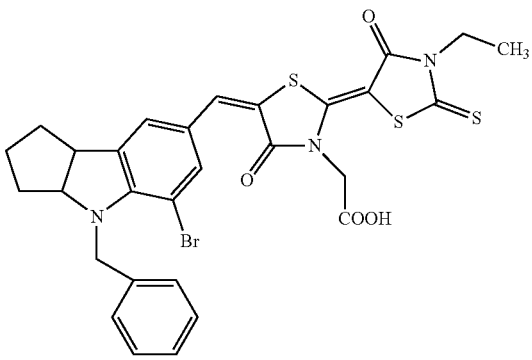
(37)
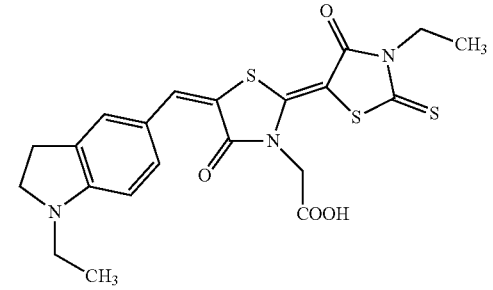
(38)
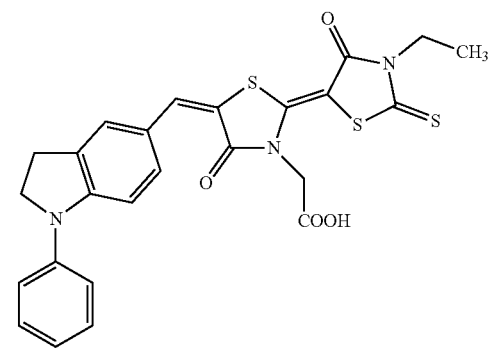
(39)
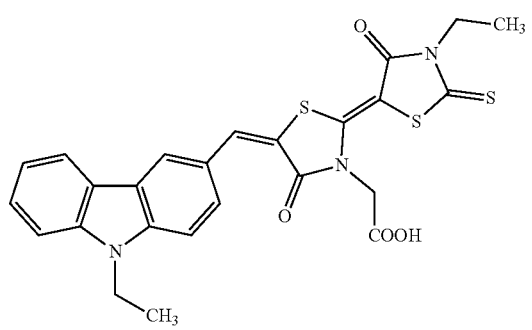
(40)

-continued

(41)
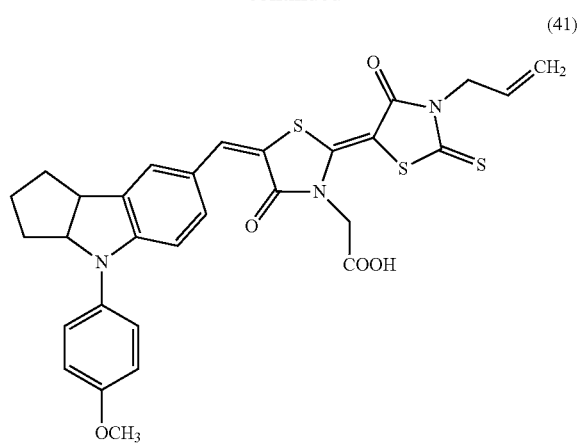

(42)
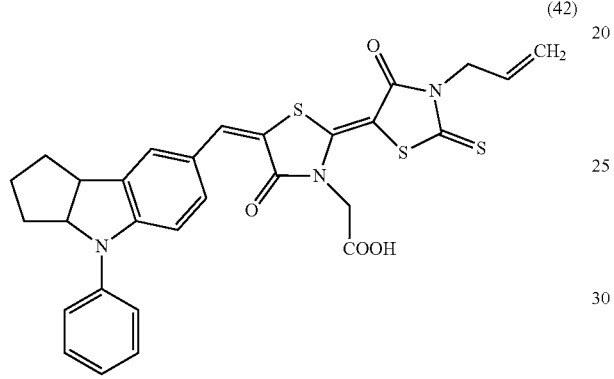

(43)
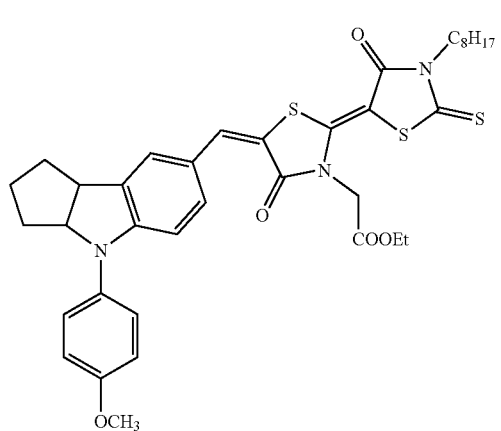

(44)
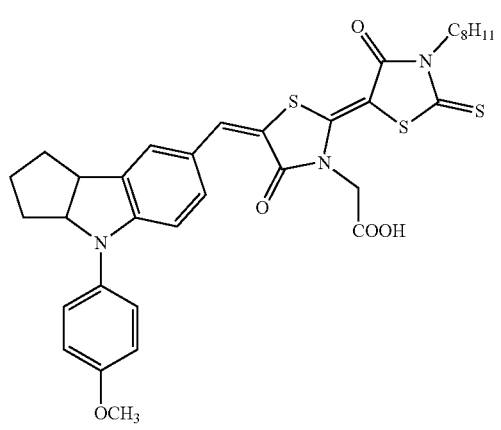

-continued

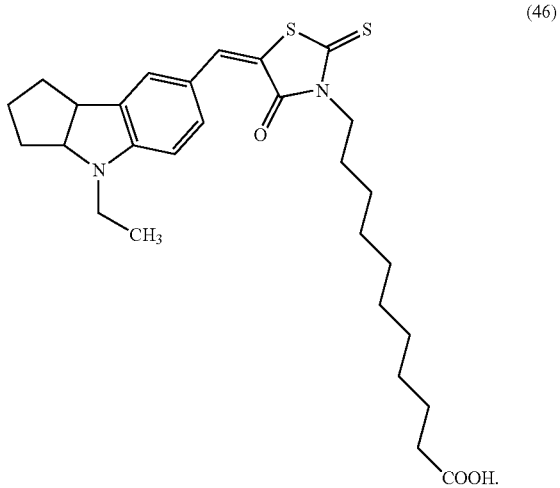

5. The method according to claim 1, wherein the transporter comprises a transporter present in one of a blood-brain barrier and a blood-cerebrospinal fluid barrier.

6. The method according to claim 1, wherein the evaluation probe serves as a substrate for the transporter or has varying permeability to the central nervous system tissue in a presence of an inhibitor for the transporter.

7. The method according to claim 6, wherein the transporter comprises one of an ABC transporter and an organic anion transporter.

8. The method according to claim 1, wherein the observing comprises obtaining signal intensity of the evaluation probe at the cranial nerve tissue as an image.

9. The method according to claim 8, wherein the image is a fluorescent image.

10. A method for evaluating an influence of a substance on a function of a transporter, wherein the transporter is associated with at least one of influx and efflux in a central nervous system, the method comprising:
  a first step of administering, to a first biological specimen, an evaluation probe as a first case in a non-invasive manner;
  independently from the first step, a second step of administering, to a second biological specimen, the evaluation probe and the substance as a second case in a non-invasive manner;
  evaluating, for the first case and the second case, a permeation of the evaluation probe through central nervous system tissue with time by measuring a fluorescence intensity derived from the evaluation probe in the central nervous system tissue multiple times with time; and
  evaluating the influence of the substance on the function of the transporter based on a change in a rate of permeation through the central nervous system tissue in the second case compared to the first case, wherein the evaluation of permeation comprises observing, more than once over time, a dyeing state of the evaluation probe at a cranial nerve tissue, and wherein the evaluation probe comprises at least one compound selected from the group consisting of compounds (1), (5)-(23), (25)-(28), and (30)-(46) and serving as a substrate for the transporter:

(1)
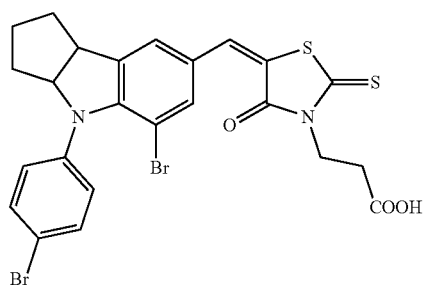

(5)
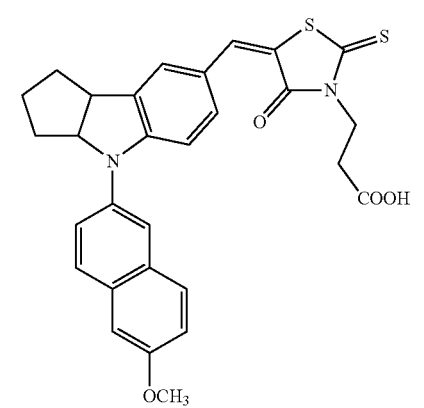

(6)
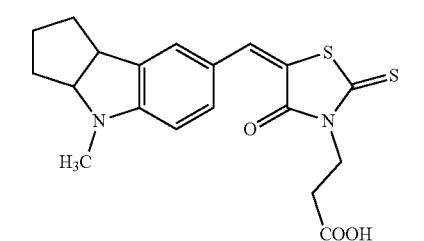

(7)
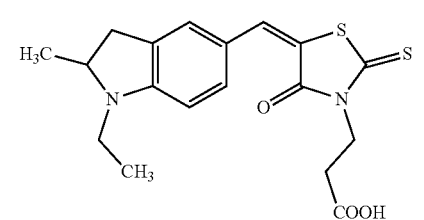

(8)
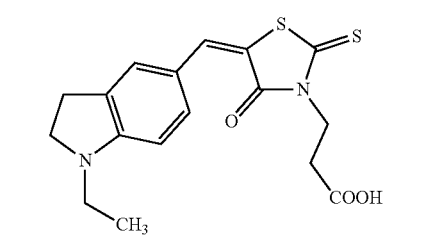

-continued (9)
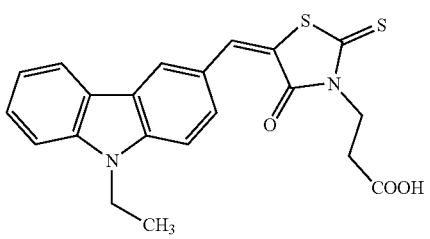

(10)
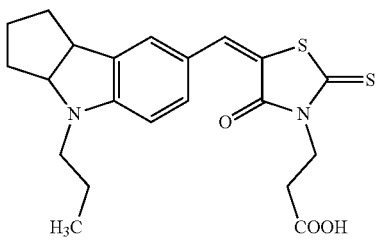

(11)
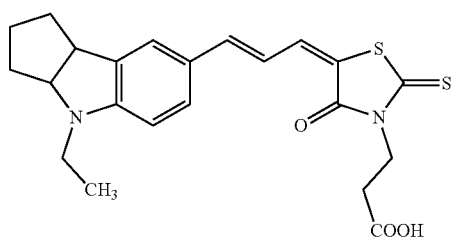

(12)
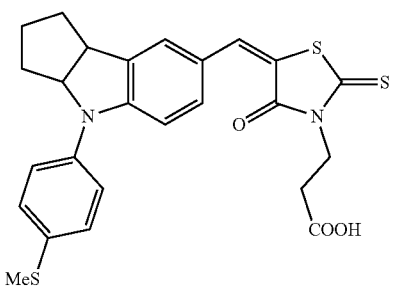

(13)
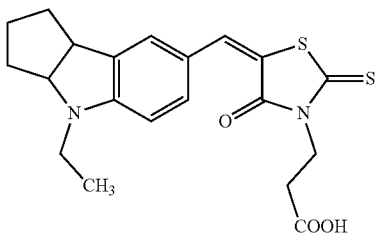

(14)
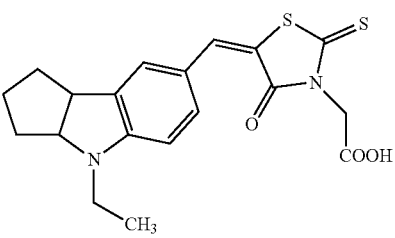

-continued
(15)
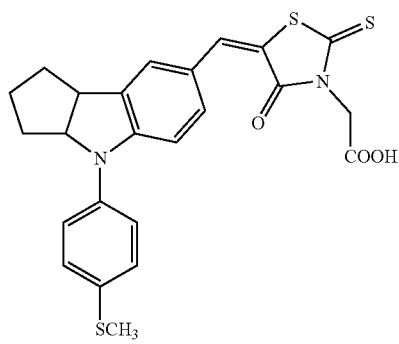
(16)
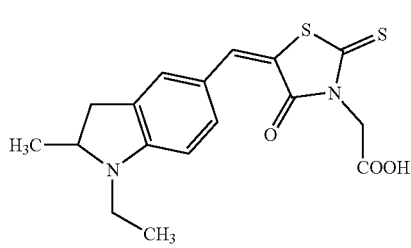
(17)
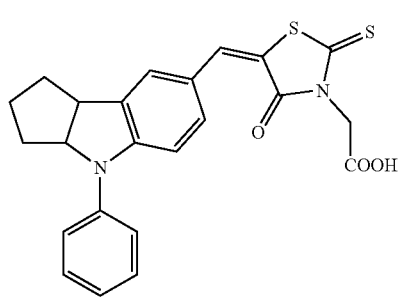
(18)
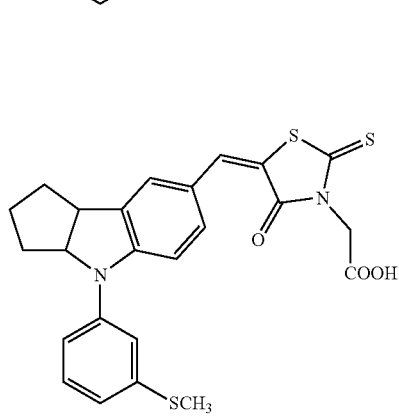
(19)
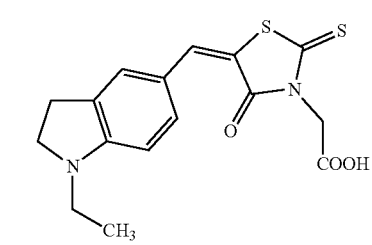
-continued
(20)
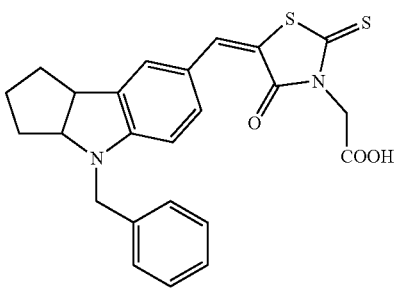
(21)
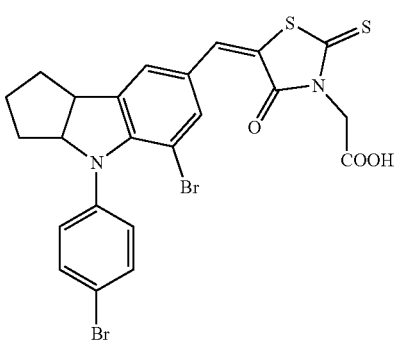
(22)
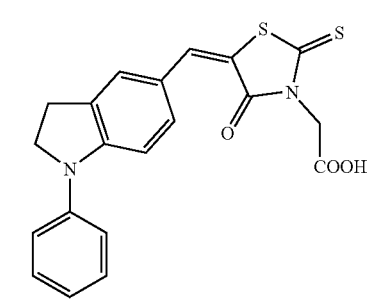
(23)
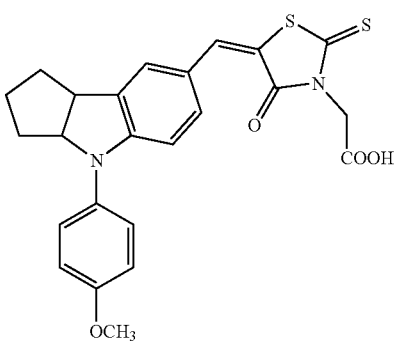
(25)
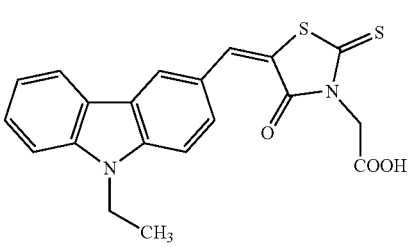

53
-continued
(26)
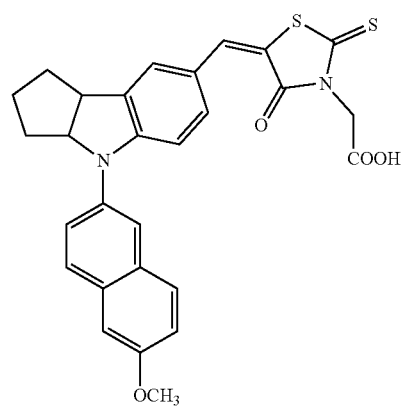
(27)
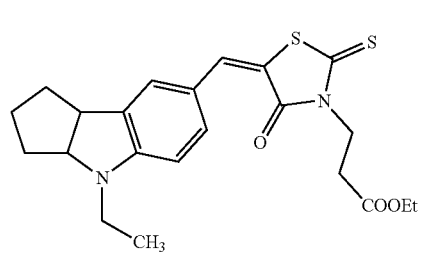
(28)
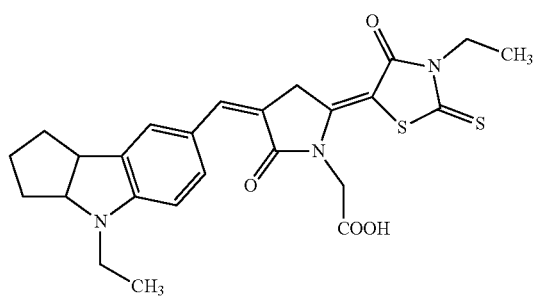
54
-continued
(31)
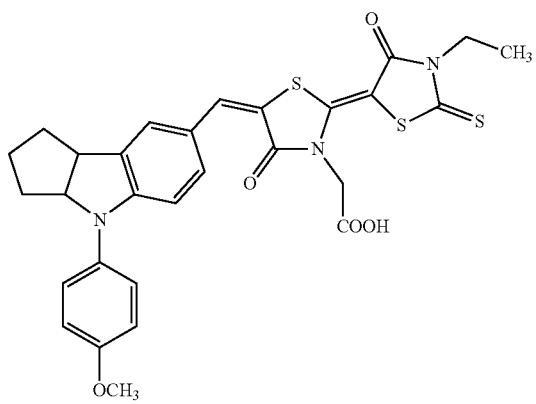
(32)
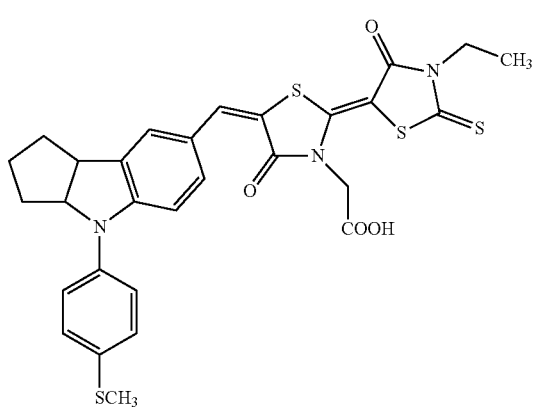
(33)
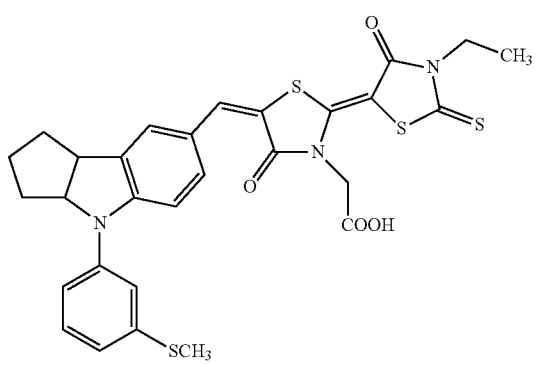

-continued
(34)
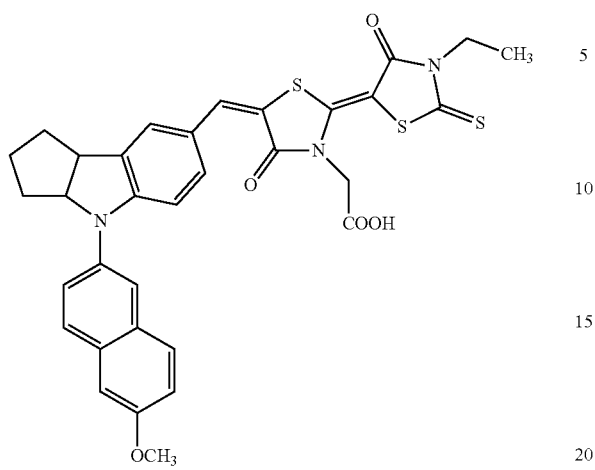
(35)
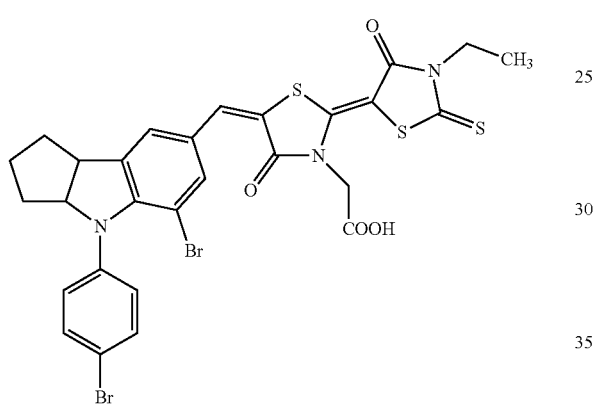
(36)
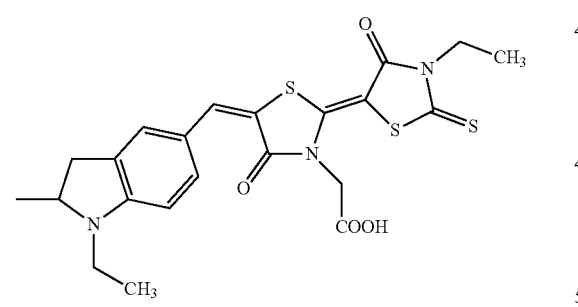
(37)
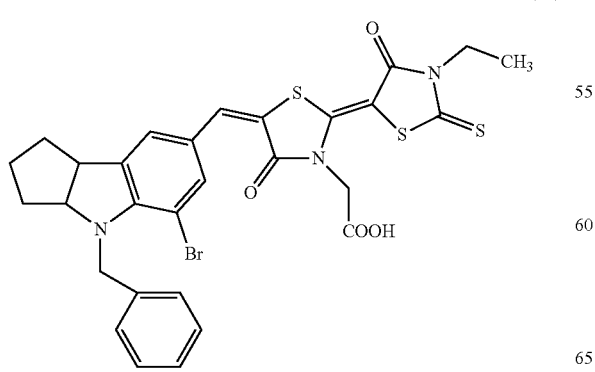
-continued
(38)
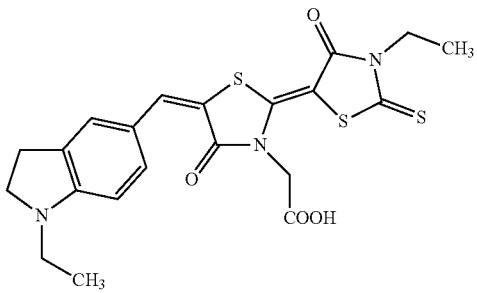
(39)
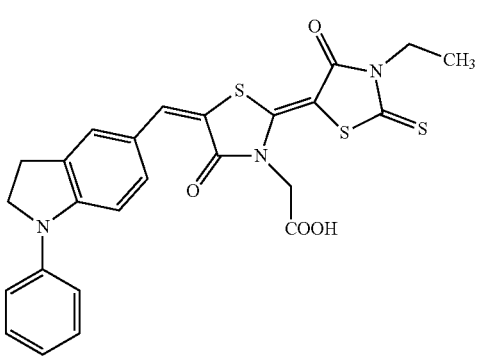
(40)
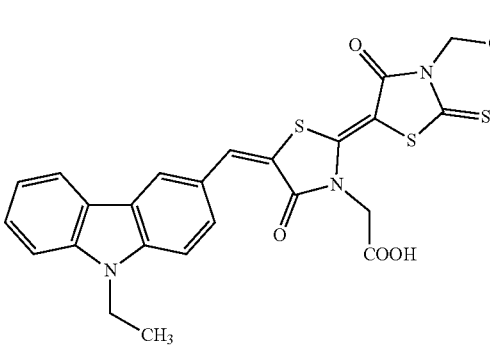
(41)
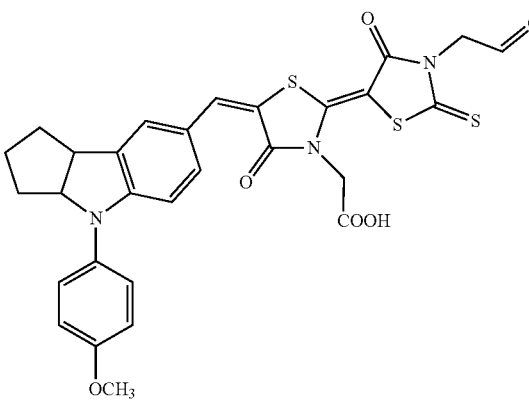

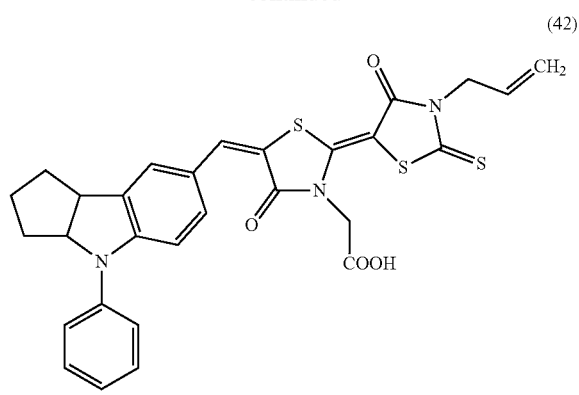
(42)

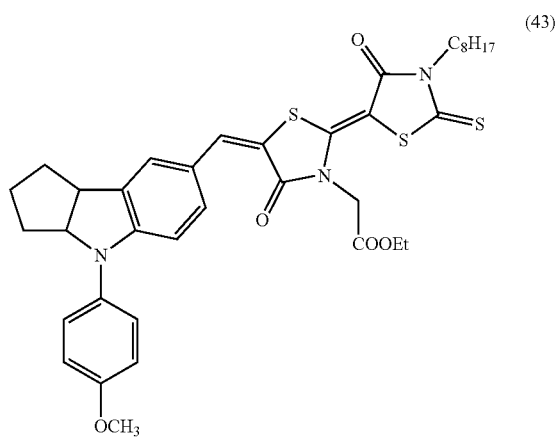
(43)

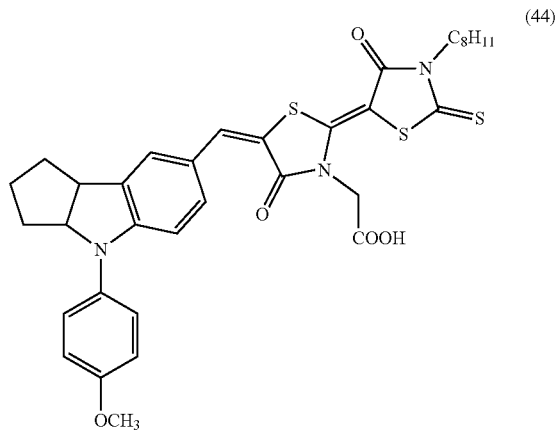
(44)

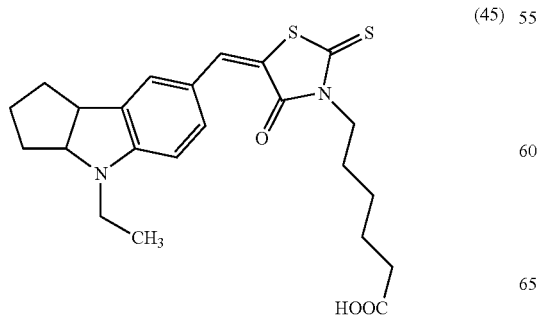
(45)

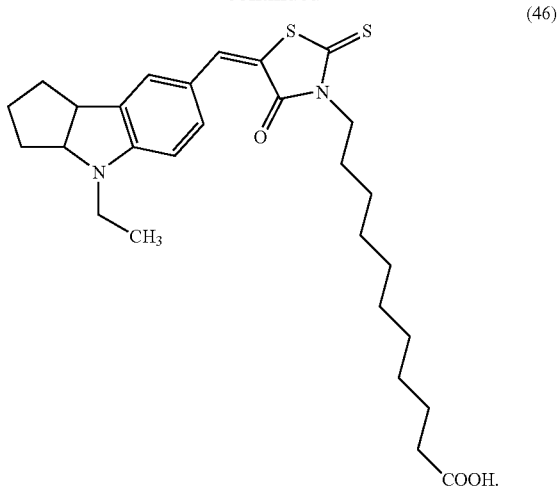
(46)

11. A screening method for a substance having an influence on a function of a transporter, wherein the transporter is associated with at least one of influx and efflux in a central nervous system, the method comprising:

a first step of administering, to a first biological specimen, an evaluation probe as a first case in a non-invasive manner;

independently from the first step, a second step of administering, to a second biological specimen, the evaluation probe and the substance as a second case in a non-invasive manner;

evaluating, for the first case and the second case, a permeation of the evaluation probe through central nervous system tissue with time by measuring a fluorescence intensity derived from the evaluation probe in the central nervous system tissue multiple times with time; and evaluating the influence of the substance on the function of the transporter based on a change in a rate of permeation through the central nervous system tissue in the second case compared to the first case, wherein the evaluation of permeation comprises observing, more than once over time, a dyeing state of the evaluation probe at a cranial nerve tissue, and wherein the evaluation probe comprises at least one compound selected from the group consisting of compounds (1), (5)-(23), (25)-(28), and (30)-(46) and serving as a substrate for the transporter:

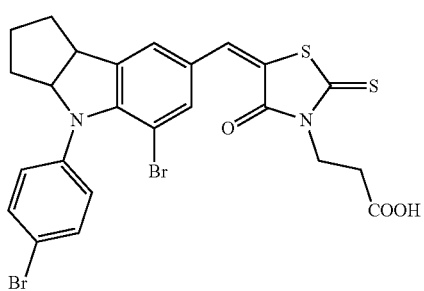
(1)

(5) 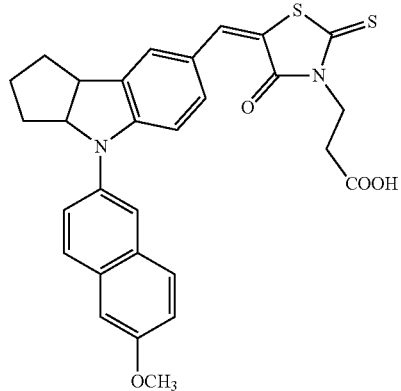
(6) 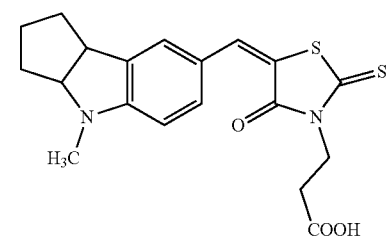
(7) 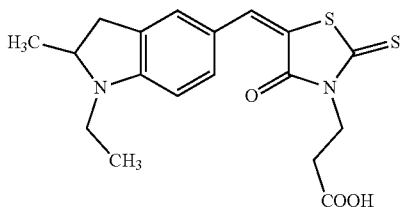
(8) 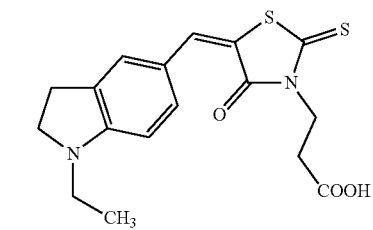
(9) 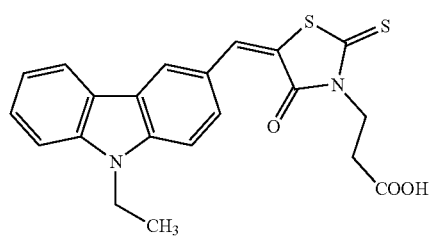
(10) 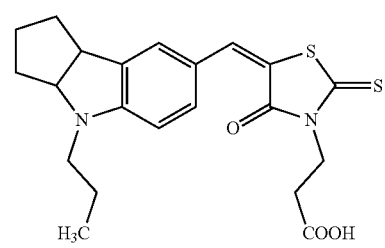
(11) 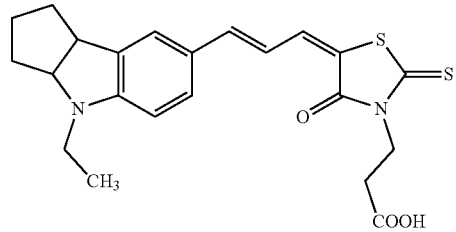
(12) 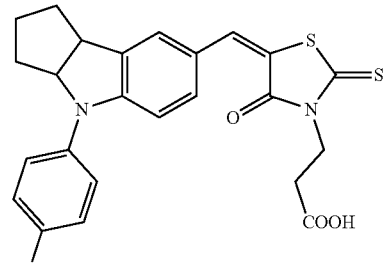
(13) 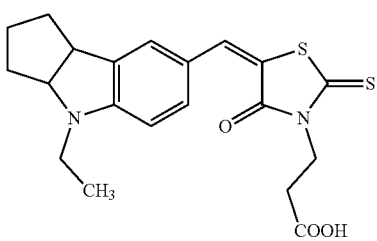
(14) 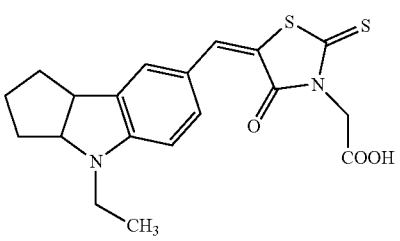
(15) 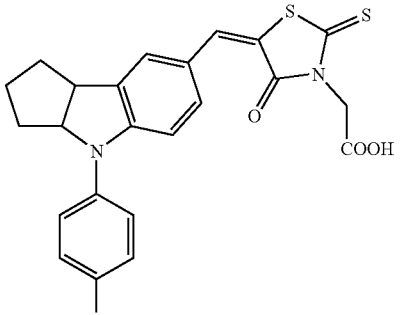
(16) 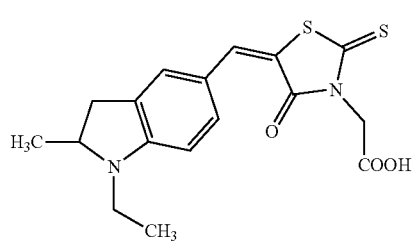

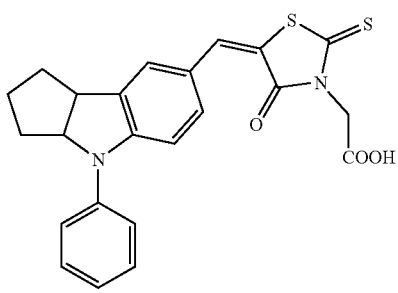 (17)
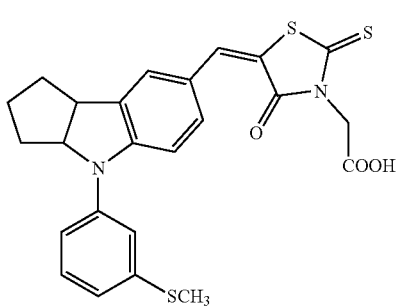 (18)
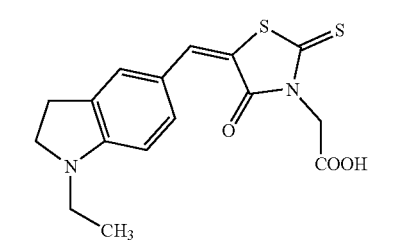 (19)
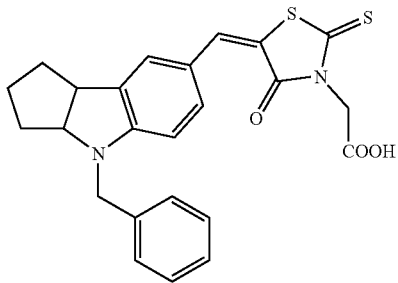 (20)
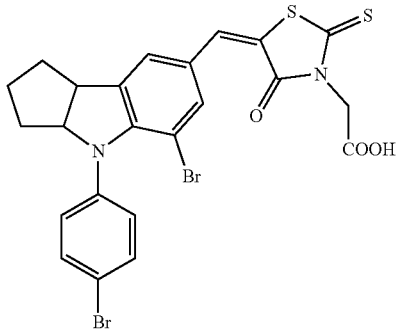 (21)
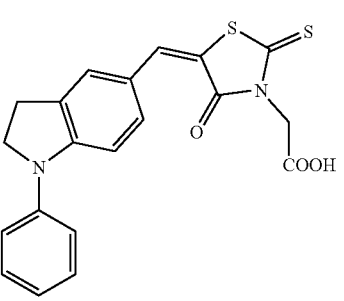 (22)
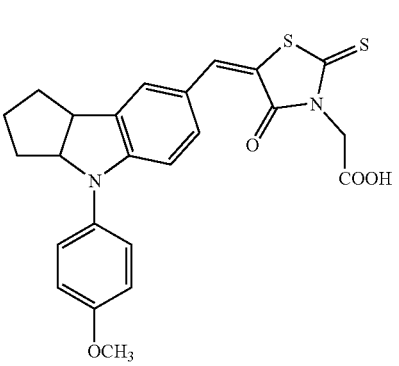 (23)
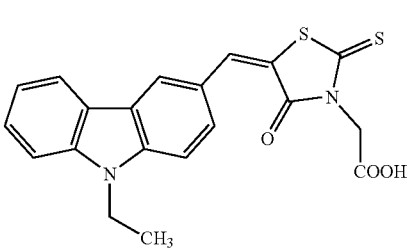 (25)
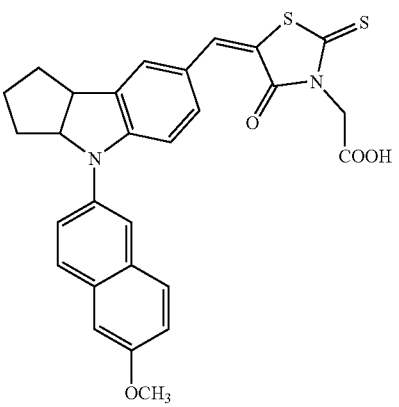 (26)
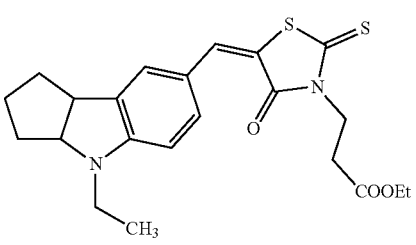 (27)

(28)
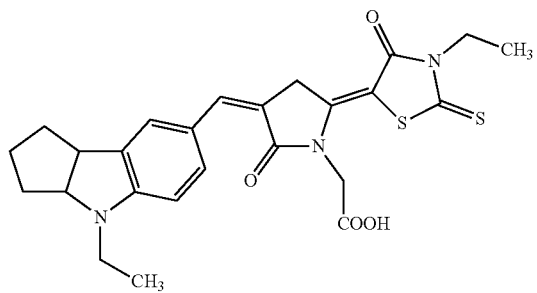
(30)
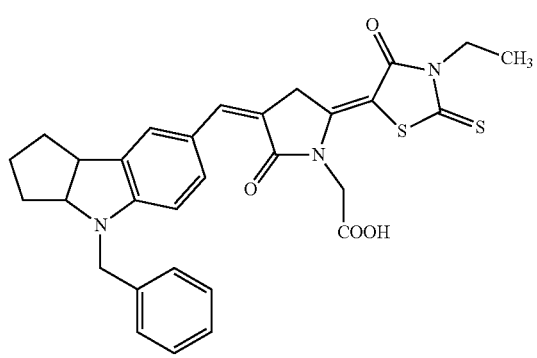
(31)
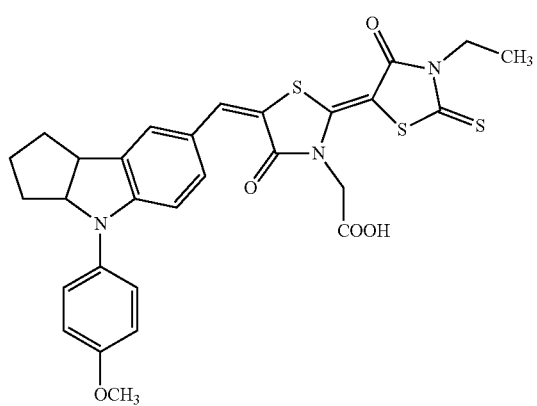
(32)
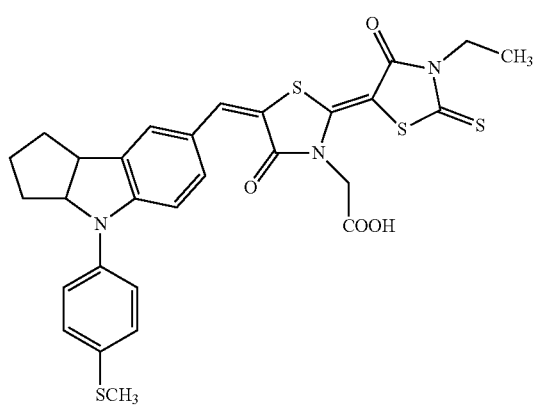
(33)
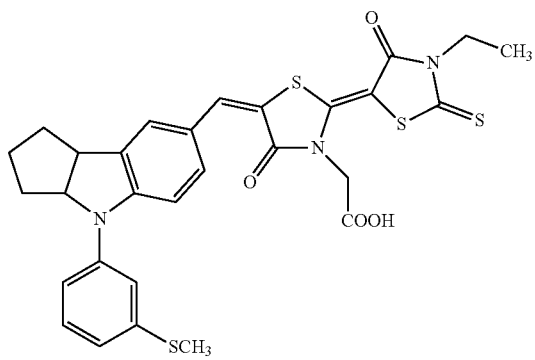
(34)
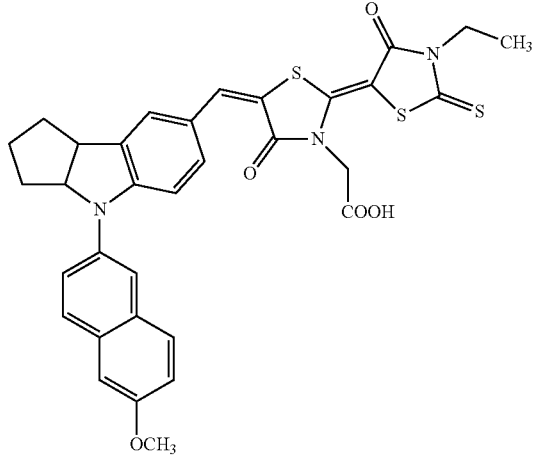
(35)
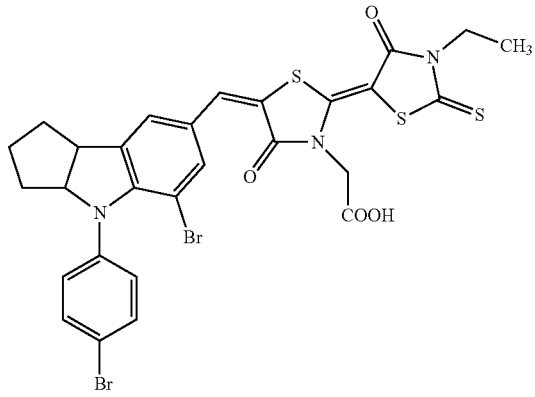
(36)
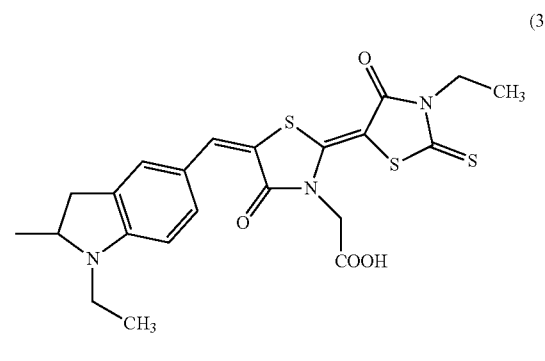

-continued
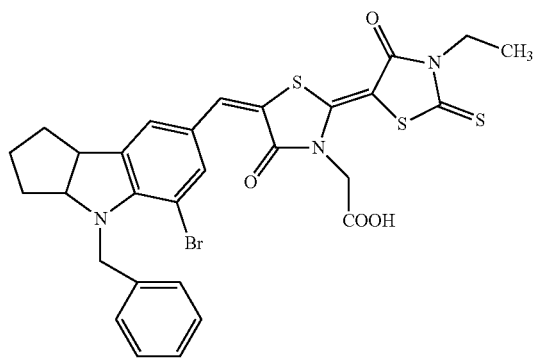
(37)
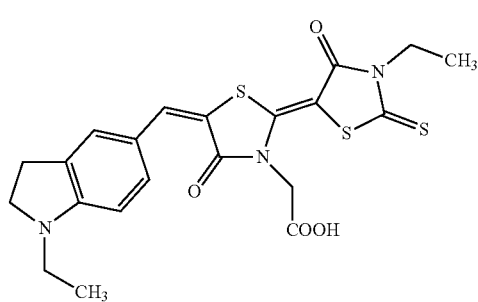
(38)
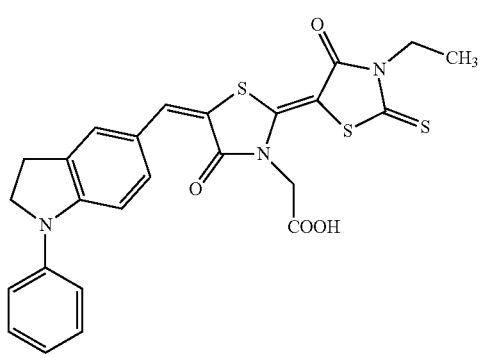
(39)
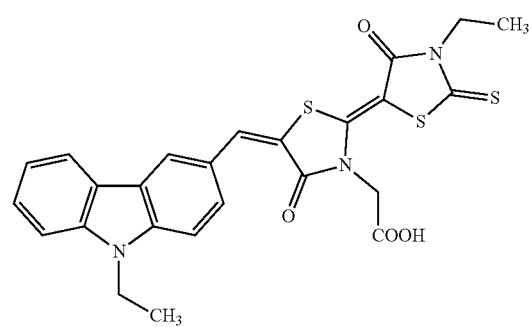
(40)
-continued
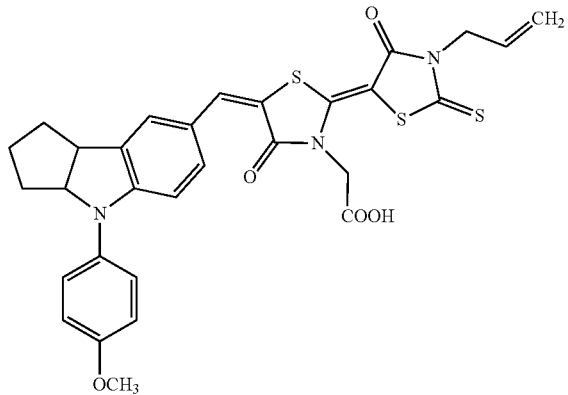
(41)
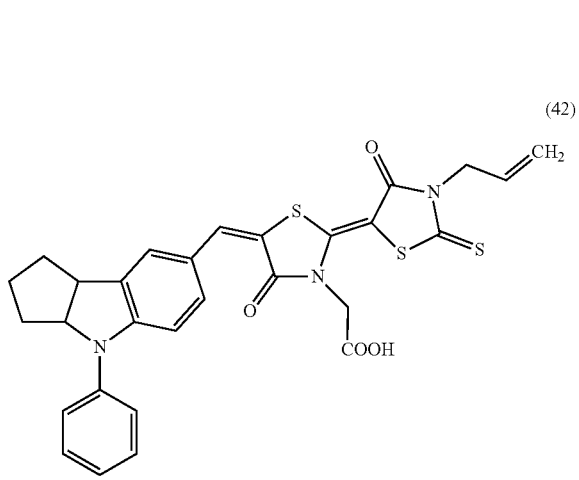
(42)
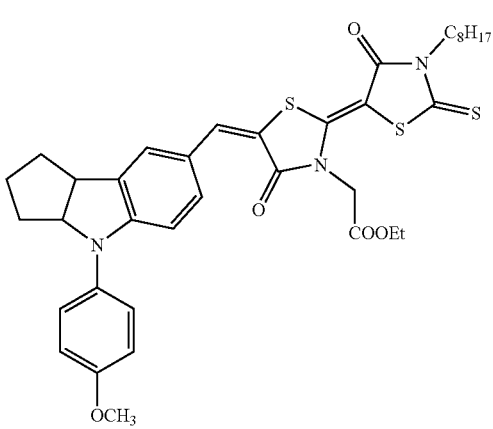
(43)

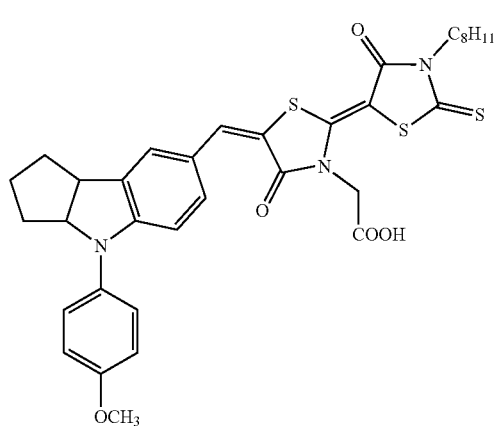
(44)
(45)
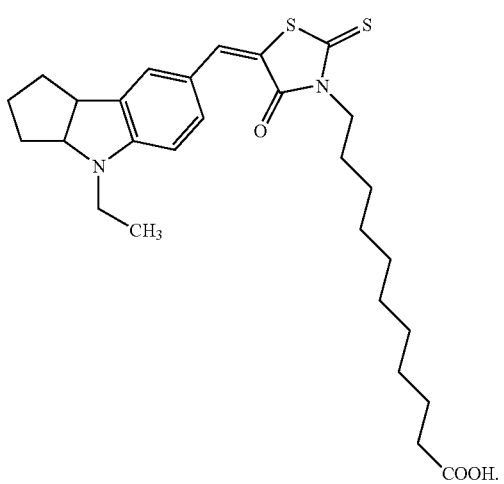
(46)
12. The method according to claim 1, wherein the evaluation probe is administered using a multiplate.
* * * * *